(12) United States Patent
Huang et al.

(10) Patent No.: US 8,377,356 B2
(45) Date of Patent: *Feb. 19, 2013

(54) METHODS FOR FABRICATING POLYMER-BIOCERAMIC COMPOSITE IMPLANTABLE MEDICAL DEVICES

(75) Inventors: Bin Huang, Pleasanton, CA (US); David C. Gale, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,518

(22) Filed: May 25, 2012

(65) Prior Publication Data

US 2012/0228810 A1    Sep. 13, 2012

Related U.S. Application Data

(62) Division of application No. 12/895,618, filed on Sep. 30, 2010, now Pat. No. 8,192,665, which is a division of application No. 11/706,550, filed on Feb. 14, 2007, now abandoned.

(51) Int. Cl.
*A61F 2/82* (2006.01)
*C08J 3/24* (2006.01)

(52) U.S. Cl. .............. 264/209.1; 523/113; 523/340

(58) Field of Classification Search .......... 264/209.1; 523/113, 340

See application file for complete search history.

(56) References Cited

U.S. PATENT DOCUMENTS

| | | | |
|---|---|---|---|
| 3,414,980 A | 12/1968 | Nezbed | |
| 3,737,337 A | 6/1973 | Schnoring et al. | |
| 4,744,365 A | 5/1988 | Kaplan et al. | |
| 5,407,609 A | 4/1995 | Tice et al. | |
| 5,626,861 A | 5/1997 | Laurencin et al. | |
| 6,007,845 A | 12/1999 | Domb et al. | |
| 6,165,486 A | 12/2000 | Marra et al. | |
| 6,395,029 B1 | 5/2002 | Levy | |
| 6,558,612 B1 | 5/2003 | Hubbard | |
| 6,689,823 B1 | 2/2004 | Bellare et al. | |
| 6,894,145 B2 | 5/2005 | Xiao et al. | |
| 7,241,856 B2 | 7/2007 | Jin et al. | |
| 7,390,335 B2 | 6/2008 | Chow | |
| 8,192,665 B2 * | 6/2012 | Huang et al. | 264/211.13 |
| 2003/0099683 A1 | 5/2003 | Grunze | |
| 2003/0134099 A1 | 7/2003 | Barrows | |
| 2005/0125054 A1 | 6/2005 | Bhat et al. | |
| 2005/0278929 A1 | 12/2005 | Lee | |
| 2006/0075921 A1 | 4/2006 | Richardson et al. | |
| 2006/0171985 A1 | 8/2006 | Richard et al. | |
| 2006/0199876 A1 | 9/2006 | Troczynski et al. | |
| 2006/0264531 A1 | 11/2006 | Zhao | |
| 2007/0026069 A1 | 2/2007 | Shastri et al. | |
| 2007/0207186 A1 | 9/2007 | Scanlon et al. | |
| 2007/0224286 A1 | 9/2007 | Kutty et al. | |
| 2007/0231365 A1 | 10/2007 | Wang et al. | |
| 2007/0282431 A1 | 12/2007 | Gale et al. | |
| 2008/0147165 A1 | 6/2008 | Hossainy et al. | |
| 2008/0306591 A1 | 12/2008 | Wang et al. | |

FOREIGN PATENT DOCUMENTS

| | | |
|---|---|---|
| JP | 40-4175213 | 6/1992 |
| JP | 41-0158485 | 6/1998 |
| JP | 2004-189868 | 7/2004 |
| JP | 2005-162970 | 6/2005 |

OTHER PUBLICATIONS

Chen et al., "Toughening of Polypropylene-Ethylene Copolymer with Nanosized $CaCO_3$ and Styrene-Butadiene-Styrene", J. of Applied Polymer Science, 94 pp. 796-802 (2004).

Lawrence E. Nielsen et al., Mechanical Properties of Polymers and Composites, 2nd ed., p. 384-385 (1993).

Thamaraiselvi et al., "Biological Evaluation of Bioceramic Materials—A Review", Trends Biomater. Artif. Organs, vol. 18(1), pp. 9-17 (2004).

Zhang et al., "Processing and properties of porous poly(L-lactide)/bioactive glass composites", Biomaterials 25, pp. 2489-2500 (2004).

\* cited by examiner

*Primary Examiner* — Tae H Yoon

(74) *Attorney, Agent, or Firm* — Squire Sanders (US) LLP

(57) ABSTRACT

Methods relating to polymer-bioceramic composite implantable medical devices are disclosed.

10 Claims, 10 Drawing Sheets

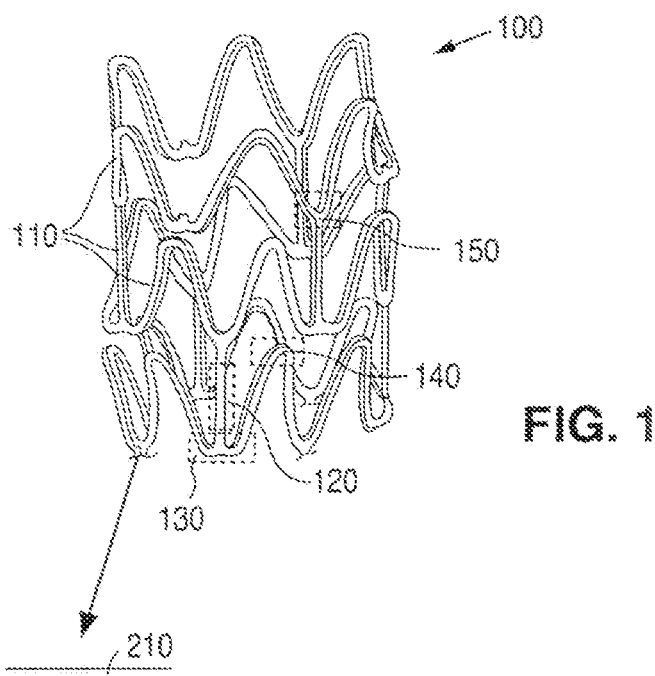
FIG. 1
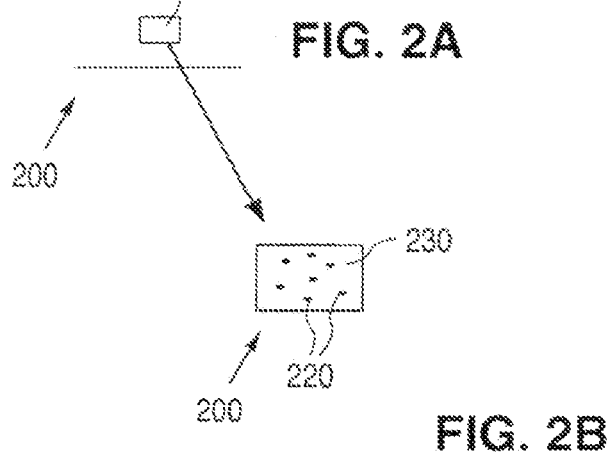
FIG. 2A
FIG. 2B
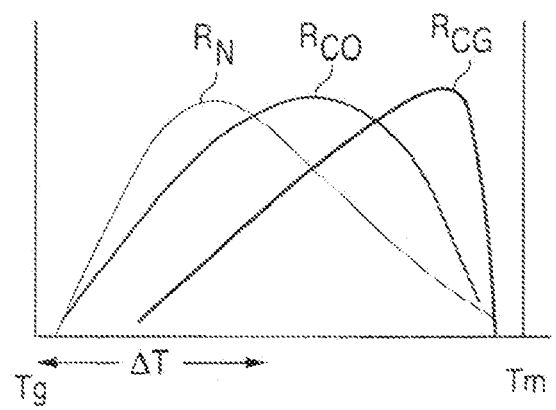
FIG. 3

METHODS FOR FABRICATING POLYMER-BIOCERAMIC COMPOSITE IMPLANTABLE MEDICAL DEVICES

CROSS REFERENCE TO RELATED APPLICATION

This application is a divisional application of U.S. patent application Ser. No. 12/895,618 which was filed on Sep. 30, 2010, now U.S. Pat. No. 8,192,665, which is a divisional of U.S. patent application Ser. No. 11/706,550 which was filed on Feb. 14, 2007, now abandoned, both of which are incorporated by reference herein.

BACKGROUND OF THE INVENTION

1. Field of the Invention

This invention relates to methods of fabricating implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

A potential problem with polymeric stents is that their struts or bar arms can crack during crimping and expansion. This is especially the case with brittle polymers. The localized portions of the stent pattern subjected to substantial deformation during crimping and expansion tend to be the most vulnerable to failure.

Therefore, it is desirable for a stent to have flexibility and resistance to cracking during deployment. It is also advantageous for a stent to be rigid and resistant to creep after deployment. It would also be desirable to be able to control the degradation rate of the device.

SUMMARY OF THE INVENTION

Various embodiments of the present invention include a method for fabricating an implantable medical device comprising: forming a suspension solution including a fluid, a polymer and bioceramic particles, wherein the polymer is dissolved in the fluid, and wherein the bioceramic particles are dispersed in the solution; evaporating at least some of the fluid to remove at least some of the polymer from the suspension solution, wherein at least some of the bioceramic particles are removed with the removal of polymer to form a composite mixture, the composite mixture comprising the removed bioceramic particles dispersed within the removed polymer; and fabricating an implantable medical device from the composite mixture.

BRIEF DESCRIPTION OF THE DRAWINGS

FIG. 1 depicts a three-dimensional view of a stent.

FIG. 2A depicts a section of a structural element from the stent depicted in FIG. 1.

FIG. 2B depicts bioceramic particles dispersed within a polymer matrix.

FIG. 3 depicts a schematic plot of the crystal nucleation rate, the crystal growth rate, and the overall rate of crystallization for a semicrystalline polymer.

DETAILED DESCRIPTION OF THE INVENTION

Figures 4A, 4B, 4C:
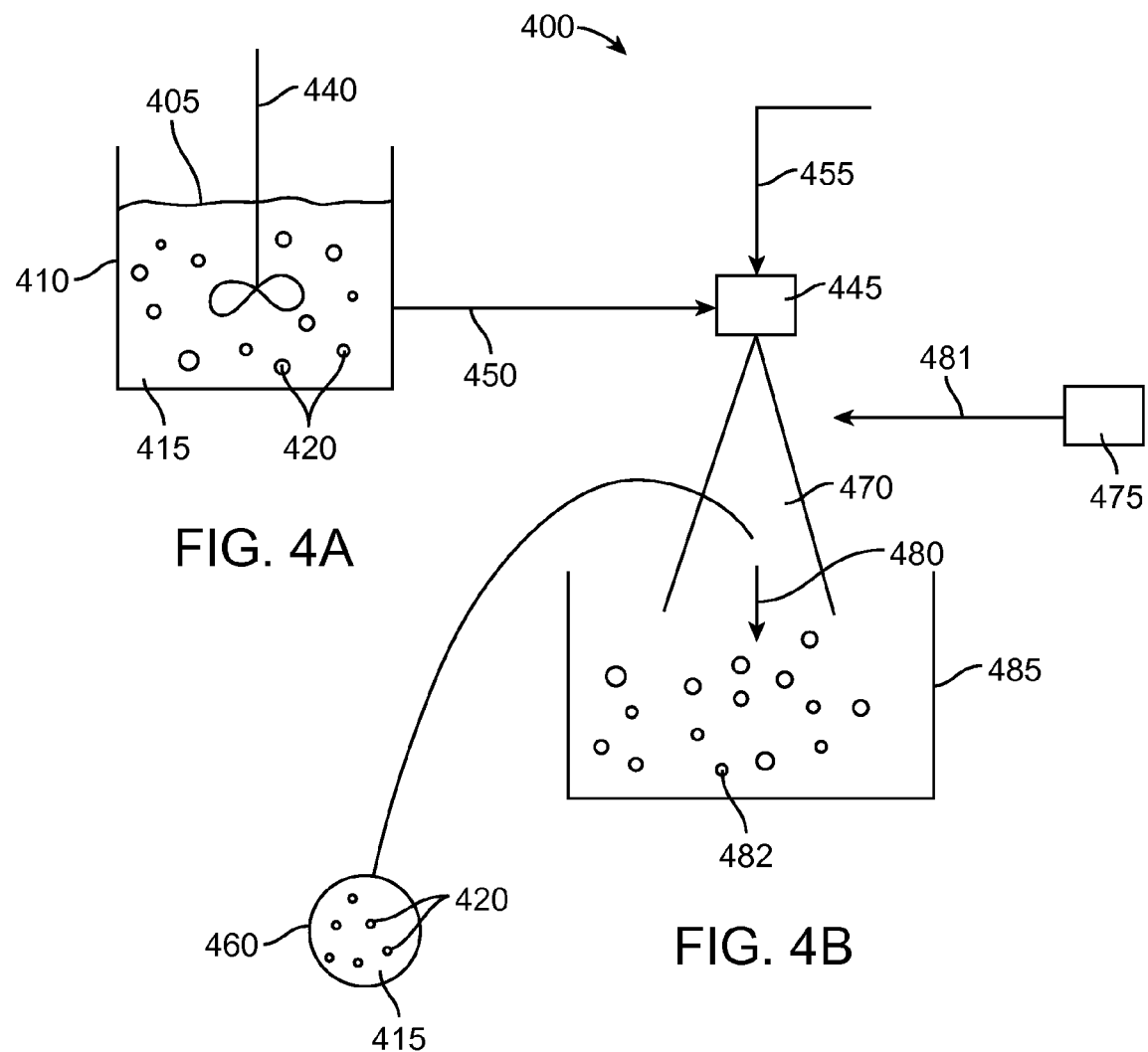
FIG. 4A-C depicts an exemplary system and process for forming a composite mixture

Those of ordinary skill in the art will realize that the following description is of the invention is illustrative only and not in any way limiting. Other embodiments of the invention will readily suggest themselves to such skilled persons based on the disclosure herein. All such embodiments are within the scope of this invention.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level. The solvent should be capable of dissolving at least 0.1 mg of the polymer in 1 ml of the solvent, and more narrowly 0.5 mg in 1 ml at ambient temperature and ambient pressure.

As used herein, an "implantable medical device" includes, but is not limited to, self-expandable stents, balloon-expandable stents, stent-grafts, implantable cardiac pacemakers and defibrillators; leads and electrodes for the preceding; implantable organ stimulators such as nerve, bladder, sphincter and diaphragm stimulators, cochlear implants; prostheses, vascular grafts, grafts, artificial heart valves and cerebrospinal fluid shunts.

An implantable medical device can be designed for the localized delivery of a therapeutic agent. A medicated implantable medical device may be constructed by coating the device with a coating material containing a therapeutic agent. The substrate of the device may also contain a therapeutic agent.

FIG. 1 depicts a three-dimensional view of stent 100. In some embodiments, a stent may include a pattern or network of interconnecting structural elements 110. Stent 100 may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1.

The embodiments are easily applicable to other patterns and other devices. The variations in the structure of patterns are virtually unlimited. A stent such as stent 100 may be fabricated from a tube by forming a pattern with a technique such as laser cutting or chemical etching.

The geometry or shape of an implantable medical device may vary throughout its structure to allow radial expansion and compression. A pattern may include portions of structural elements or struts that are straight or relatively straight, an example being a portion 120. In addition, patterns may include structural elements or struts that include curved or bent portions such as portions 130, 140, and 150.

An implantable medical device can also be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

However, polymers tend to have a number of shortcomings for use as materials for implantable medical devices such as stents. Many biodegradable polymers have a relatively low modulus at the physiological conditions in the human body. In general, compared to metals, the strength to weight ratio of polymers is smaller than that of metals. A polymeric stent with inadequete radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under physiological conditions or conditions within a human body. Specifically, such polymers can have a Tg above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent.

Other potential problems with polymeric stents include creep, stress relaxation, and physical aging. Creep refers to the gradual deformation that occurs in a polymeric construct subjected to an applied load. Creep occurs even when the applied load is constant.

It is believed that the delayed response of polymer chains to stress during deformation causes creep behavior. As a polymer is deformed, polymeric chains in an initial state rearrange to adopt a new equilibrium configuration. Rearrangement of chains takes place slowly with the chains retracting by folding back to their initial state. For example, an expanded stent can retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation.

Physical aging, as used herein, refers to densification in the amorphous regions of a semi-crystalline polymer. Densification is the increase in density of a material or region of a material. Densification, and thus physical aging, is also the result of relaxation or rearrangement of polymer chains.

Various embodiments of the present invention include an implantable medical device fabricated from a composite including a polymer matrix or continuous phase and bioceramic particles as a discrete phase. The bioceramic particles may tend to reduce or eliminate a number of the above-mentioned shortcomings of polymers. For example, the bioceramic particles can increase the toughness and modulus and modify the degradation rate of the polymer. In some embodiments, the composite may include a plurality of bioceramic particles dispersed within the polymer.

In general, it is desirable for the bioceramic particles to be uniformly dispersed throughout the biodegradable polymer. The more uniform the dispersion of the particles results in more uniform properties of the composite and a device fabricated from the composite. For example, a uniform dispersion can result in a uniform increase in toughness and modulus and modification of degradation rate. In some embodiments, the bioceramic particles are uniformly or substantially uniformly dispersed within the biodegradable polymer.

In certain embodiments, a structural element of an implantable medical device may be fabricated from a bioceramic/polymer composite. Structural elements can include, but are not limited to, any supporting element such as a strut, wire, or filament. FIG. 2A depicts a section 200 of a structural element 110 from stent 100. A portion 210 of section 200 is shown in an expanded view in FIG. 2B. FIG. 2B depicts bioceramic particles 220 dispersed throughout a polymer matrix 230.

Bioceramics can include any ceramic material that is compatible with the human body. More generally, bioceramic materials can include any type of compatible inorganic material or inorganic/organic hybrid material. Bioceramic materials can include, but are not limited to, calcium sulfate, alumina, zirconia, apatites, calcium phosphates, silica based glasses, or glass ceramics, and pyrolytic carbons. Bioceramic materials can be bioabsorbable and/or active. A bioceramic is active if it actively takes part in physiological processes. A bioceramic material can also be "inert," meaning that the material does not absorb or degrade under physiological conditions of the human body and does not actively take part in physiological processes.

Illustrative examples of apatites and other calcium phosphates, include, but are not limited hydroxyapatite ($Ca_{10}(PO_4)_6(OH)_2$), floroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)6-5H_2O$), octacalcium phosphate ($Ca_8H_2(PO_4)6-5H_2O$), calcium pyrophosphate ($Ca_2P_2O_7.2H_2O$), tetracalcium phosphate ($Ca_4P_2O_9$), and dicalcium phosphate dehydrate ($CaHPO_4.2H_2O$).

The term bioceramics can also include bioactive glasses that are bioactive glass ceramics composed of compounds such as $SiO_2$, $Na_2O$, $CaO$, and $P_2O_5$. For example, a commercially available bioactive glass, Bioglass®, is derived from certain compositions of $SiO_2$—Na2O—$K_2O$—CaO—MgO—$P_2O_5$ systems. Some commercially available bioactive glasses include, but are not limited to:

45S5: 46.1 mol % SiO2, 26.9 mol % CaO, 24.4 mol % $Na_2O$ and 2.5 mol % $P_2O_5$;

58S: 60 mol % SiO2, 36 mol % CaO, and 4 mol % $P_2O_5$; and

S70C30: 70 mol % SiO2, 30 mol % CaO.

Another commercially available glass ceramic is A/W.

In some embodiments, bioceramic particles in a composite implantable medical device may be used to inhibit or prevent infection since some bioceramics can have an anti-infective property. Bioceramics may release various ions such as calcium and phosphate ions which broadly exist in human body fluid and blood plasma. Examples of bioceramics that release calcium and/or phosphate ions include various calcium phosphates and bioactive glasses. The released ions may depress foreign body reaction. Trends Biomater. Artif. Tren, Vol 18 (1), pp 9-17.

As indicated above, an implantable medical device such as a stent can be medicated by incorporating an active agent in a coating over the device or within the substrate of the device. In some embodiments, the ions released from bioceramics can have an additive therapeutic and/or a synergistic therapeutic effect to the active agent. For example, ions can be used in conjunction with anti-proliferative and/or anti-inflammatory agents.

Bioceramic particles can be partially or completely made from a biodegradable, bioabsorbable, or biostable ceramic. Examples of bioabsorbable bioceramics include various types of bioglass materials, tetracalcium phosphate, amorphous calcium phosphate, alpha-tricalcium phosphate, and beta-tricalcium phosphate. Biostable bioceramics include alumina and zirconia.

Various sizes of the bioceramic particles may be used in the composite. For example, the bioceramic particles can include, but are not limited to, nanoparticles and/or micro particles. A nanoparticle refers to a particle with a characteristic length (e.g., diameter) in the range of about 1 nm to about 1,000 nm. A micro particle refers to a particle with a characteristic length in the range of greater than 1,000 nm and less than about 10 micrometers. Additionally, bioceramic particles can be of various shapes, including but not limited to, spheres and fibers.

Additionally, the particles size distribution can be important in modifying the properties of the polymer. Generally, a narrow size distribution is preferable.

The composite of a structural element of a device may have between 0.01% and 10% of bioceramic particles by weight, or more narrowly, between 0.5% and 2% bioceramic particles by weight as compared to the polymer matrix of the composite.

As indicated above, the bioceramic particles can reduce or eliminate a number of shortcomings of polymers that are used for implantable medical devices. In one aspect of the invention, bioceramic particles can increase the fracture toughness of polymers of implantable medical device. In general, the higher the fracture toughness, the more resistant a material is to the propagation of cracks. In some embodiments, bioceramic particles may be used in a composite having a matrix polymer that is brittle at physiological conditions. In particular, such a polymer can have a Tg above body temperature. In one embodiment, the bioceramic particles may be nanoparticles.

Certain regions of an implantable medical device, such as a stent, experience a high degree of stress and strain when the device is under stress during use. For example, when a stent is crimped and deployed, curved or bending regions such as portions 130, 140, and 150 can have highly concentrated strain which can lead to fracture. The bioceramic particles can increase fracture toughness by reducing the concentration of strain by dispersing the strain over a large volume of the material. Particles can absorb energy due to applied stress and disperse energy about a larger volume in the bioceramic/polymer composite.

Therefore, rather than being highly concentrated the stress and strain in a device fabricated from a bioceramic composite is divided into many small interactions involving numerous individual particles. When a crack is initiated in the material and starts traveling through the composite, the crack breaks up into finer and finer cracks due to interaction with the particles. Thus, the particles tend to dissipate the energy of imparted to the device by the applied stress. In general, the increase in the toughness is directly proportional to the size of the particles. For a give weight ratio of particles to matrix, as the size of the particles decreases the number of particles dispersed throughout the device per unit volume also increases. Thus, the number of particles to disperse the energy of applied stress to the device increases. Therefore, it is advantageous to use nanoparticles to increase the toughness of the polymer. It has been shown that the fracture toughness of a polymeric material can be improved by using nanoparticles as a discrete or reinforcing phase in a composite. J. of Applied Polymer Science, 94 (2004) 796-802.

Bioceramic particles, more particularly nano-bioceramic particles, by providing more crystallites in a network in the bioceramic/polymer composite increase fracture toughness.

In yet another aspect of the invention, bioceramic particles can be used to increase the modulus of the polymer. As indicated above, a polymeric stent requires a high radial strength in order to provide effective scaffolding of a vessel. Many biodegradable polymers have a relatively low modulus as compared to metals. A composite with bioceramic particles with a higher modulus than a matrix polymer may have a higher modulus than the polymer. The higher modulus may allow for the manufacture of a composite stent with much thinner struts than a stent fabricated from the matrix polymer alone. Examples of relatively low modulus polymers include, but are not limited to, poly(D,L-lactide-co-glycolide), poly (lactide-co-caprolactone), poly(lactide-co-trimethylene carbonate), poly(glycolide-co-caprolactone), and poly(D,L-lactide). It has been reported that composites with nanoparticles can increase the modulus of a polymer by 1-2 orders of magnitude. Mechanical Properties of Polymers and Composites, Lawrence E. Nielsen and Robert F. Landel, $2^{nd}$ ed., p. 384-385 (1993).

In addition, bioceramic particles in a polymer composite can also reduce or eliminate creep, stress relaxation, and physical aging. It is believed that particles can act as "net point" that reduce or inhibit movement of polymer chains in amorphous regions of a polymer.

Additionally, in composites fabricated from semicrystalline polymers, the crystallinity of a bioceramic/polymer composite that forms an implantable device can be controlled to reduce or eliminate creep, stress relaxation, and physical aging. As indicated above, these phenomena in a polymer are due to rearrangement or relaxation of polymer chains.

In general, as the crystallinity of a semicrystalline polymer increases, physical aging creep, and stress relaxation are reduced. This is likely due to the fact that polymer chains in the amorphous domains capable of movement are reduced by the crystalline domains. However, increasing crystallinity can result in brittleness in a polymer at physiological conditions.

In further embodiments, a structural element of an implantable medical device may include a composite having a plurality of crystalline domains dispersed within an amorphous biodegradable polymeric matrix phase. The crystalline domains may be formed around bioceramic particles. In certain embodiments, the composite that makes up the structural element may have a relatively low crystallinity. For example, the crystallinity can be less than 50%, 30%, 20%, or less than 10%.

Additionally, the device can be fabricated so that the resulting composite has a relatively large number of crystalline domains that are relatively small. In certain embodiments, the average crystal size can be less than 10 microns, 5 microns, or less than 2 microns. As the size of the crystalline domains decreases along with an increase in the number of domains, the polymer may become less brittle and, which increases the fracture toughness. Although the crystallinity of the resulting polymer can be relatively low, the presence of the relatively large number of relatively small crystalline domains can reduce or eliminate physical aging, creep, and stress relaxation.

The size and number of crystallites domains can be controlled during formation of a polymer construct from an implantable medical device is fabricated. Polymer constructs, such as tubes, can be formed using various types of forming methods, including, but not limited to extrusion or injection molding. Representative examples of extruders include, but are not limited to, single screw extruders, intermeshing co-rotating and counter-rotating twin-screw extruders, and other multiple screw masticating extruders.

In some embodiments, a mixture of a polymer and bioceramic particles can be extruded to form a polymer construct, such as a tube. A polymer melt mixed with the bioceramic particles can be conveyed through an extruder and forced through a die in the shape of as an annular film in the shape of a tube. The annular film can be cooled below the melting point, Tm, of the polymer to form an extruded polymeric tube. For example, the annular film may be conveyed through a water bath at a selected temperature. Alternatively, the annular film may be cooled by a gas at a selected temperature. The annular film may be cooled at or near an ambient temperature, e.g. 25° C. Alternatively, the annular film may be cooled at a temperature below ambient temperature.

In general, crystallization in a polymer tends to occur in a polymer at temperatures between Tg and Tm of the polymer. Therefore, in some embodiments, the temperature of the polymer construct during cooling can be between Tg and Tm. As the temperature of the extruded mixture is cooled below Tm to form a polymer construct, such as a tube, the bioceramic particles provide a point of nucleation in the polymer melt for the formation of crystalline domains.

A network of many small crystalline domains is formed, which can work to tie crystalline domains together and reduce, inhibit or prevent fracturing, creep, stress relaxation, and physical aging of the polymer. The crystalline domains can serve as net points in the amorphous domains that restrict the freedom of movement of polymer chains in the amorphous domain. As a result, physical aging, creep, and stress relaxation can be reduced. In addition, for the reasons discussed above, the toughness of the polymer is also increased.

In general, both microparticles and nanoparticles can be used as nucleation points. However, as the number of particles increases and size of the particles decreases, the crystalline domains become more effective in increasing fracture toughness and reducing physical aging, creep, and stress relaxation. The closer the crystalline domains are to one another within the amorphous domain of a polymer, the more the crystalline domains can limit the degree of freedom movement of polymer chains in the amorphous domain. Therefore, nanoparticles may be more effective in reducing physical aging, creep, and stress relaxation.

In certain embodiments, the size of the crystalline domains can be controlled by the temperature of the cooling polymer construct from an extruder. In general, crystallization tends to occur in a polymer at temperatures between Tg and Tm of the polymer. The rate of crystallization in this range varies with temperature. FIG. 3 depicts a schematic plot of the crystal nucleation rate ($R_N$), the crystal growth rate ($R_{CG}$), and the overall rate of crystallization ($R_{CO}$). The crystal nucleation rate is the growth rate of new crystals and the crystal growth rate is the rate of growth of formed crystals. The overall rate of crystallization is the sum of curves $R_N$ and $R_{CG}$.

In certain embodiments, the temperature of the cooling polymer construct can be at a temperature at which the overall crystallization rate is relatively low. At such a temperature, the increase in crystallinity is predominantly due to formation of crystalline domains around the bioceramic particles, rather than the growth of existing crystals. In some embodiments, the temperature can be in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, 50, 100, or greater than 100. In another embodiment, the temperature range may be in range, $\Delta T$, shown in FIG. 3, between about Tg to about 0.25(Tm−Tg)+Tg.

In general, good bonding between a continuous phase and a discrete or reinforcing phase in a composite material facilitates improvement of the mechanical performance of the composite. For example, increase of the modulus and fracture toughness of a polymer due to a bioceramic particle phase can be enhanced by good bonding between the polymer and particles.

In some embodiments, bioceramic particles may include an adhesion promoter to improve the adhesion between the particles and the polymer matrix. In one embodiment, an adhesion promoter can include a coupling agent. A coupling agent refers to a chemical substance capable of reacting with both the bioceramic particle and the polymer matrix of the composite material. A coupling agent acts as an interface between the polymer and the bioceramic particle to form a chemical bridge between the two to enhance adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes. In particular, 3-aminopropyltrimethoxysilane has been shown to facilitate adhesion between poly(L-lactide) and bioglass. Biomaterials 25 (2004) 2489-2500.

In some embodiments, the surface of the bioceramic particles may be treated with an adhesion promoter prior to mixing with the polymer matrix. In one embodiment, the bioceramic particles can be treated with a solution containing the adhesion promoter. Treating can include, but is not limited to, coating, dipping, or spraying the particles with an adhesion promoter or a solution including the adhesion promoter. The particles can also be treated with a gas containing the adhesion promoter. In one embodiment, treatment of the bioceramic particles includes mixing the adhesion promoter with solution of distilled water and a solvent such as ethanol and then adding bioceramic particles. The bioceramic particles can then be separated from the solution, for example, by a centrifuge, and the particles can be dried. The bioceramic particles may then used to form a polymer composite. In an alternative embodiment, the adhesion promoter can be added to the particles during formation of the composite. For example, the adhesion promoter can be mixed with a bioceramic/polymer mixture during extrusion.

As indicated above, a device may be composed in whole or in part of materials that degrade, erode, or disintegrate through exposure to physiological conditions within the body until the treatment regimen is completed. The device may be configured to disintegrate and disappear from the region of implantation once treatment is completed. The device may disintegrate by one or more mechanisms including, but not limited to, dissolution and chemical breakdown.

The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months. Thus, it is desirable for an implantable medical device, such as a stent, to have a degradation time at or near the duration of treatment. Degradation time refers to the time for an implantable medical device to substantially or completely erode away from an implant site.

Several mechanisms may be relied upon for erosion and disintegration of implantable devices which include, but are not limited to, mechanical, chemical breakdown and dissolution. Therefore, bodily conditions can include, but are not limited to, all conditions associated with bodily fluids (contact with fluids, flow of fluids) and mechanical forces arising from body tissue in direct and indirect contact with a device. Degradation of polymeric materials principally involves chemical breakdown involving enzymatic and/or hydrolytic cleavage of device material due to exposure to bodily fluids such as blood.

Chemical breakdown of biodegradable polymers results in changes of physical and chemical properties of the polymer, for example, following exposure to bodily fluids in a vascular environment. Chemical breakdown may be caused by, for example, hydrolysis and/or metabolic processes. Hydrolysis is a chemical process in which a molecule is cleaved into two parts by the addition of a molecule of water. Consequently, the degree of degradation in the bulk of a polymer is strongly dependent on the diffusivity, and hence the diffusion rate of water in the polymer.

Another deficiency of some biodegradable polymers, such as poly(L-lactide), is that the degradation rate is slow and results in a degradation time of a stent outside of the desired range. A preferred degradation is from six to twelve months. Increasing the equilibrium content of moisture in a biodegradable polymer that degrades by hydrolysis can increase the degradation rate of a polymer. Various embodiments of the present invention include increasing the equilibrium moisture content in a polymer of a device to accelerate the degradation rate.

In some embodiments, bioabsorbable bioceramic particles may be included in a bioceramic/polymer composite device to increase the degradation time of the polymer of the device. In an embodiment, the degradation rate of a bioceramic/polymer composite device can be tuned and/or adjusted to a desired time frame. As the bioceramic particle erodes within the polymeric matrix, the porosity of the matrix increases. The increased porosity increases the diffusion rate of moisture through the polymeric matrix, and thus, the equilibrium moisture content of the polymeric matrix. As a result, the degradation rate of the polymer is increased. The porous structure also increases the transport of degradation products out of the matrix, which also increases the degradation rate of the matrix.

In certain embodiments, the degradation rate and degradation time of the device can be tuned or controlled through variables such as the type of bioceramic material and the size and shape of particles. In some embodiments, bioceramic materials can be selected to have a higher degradation rate than the polymer matrix. The faster the degradation rate of the bioceramic material, the faster the porosity of the polymer matrix increases which results in a greater increase in the degradation rate of the polymer matrix. Additionally, the size of the particles influence the time for erosion of the particles. The smaller the particles, the faster the erosion of the particles because of the higher surface area per unit mass of particles.

For example, nanoparticles may have a relatively fast erosion rate compared to microparticles. Additionally, elongated particles, such as fibers, may tend to erode faster on a per unit mass basis due to the higher surface area per unit mass of the particle. Also, short fibers may tend to erode faster than longer fibers. Short fibers refer to long fibers than have been cut into short lengths. In some embodiments, the short fibers may be made by forming fibers as described above, and cutting them into short lengths. In one embodiment, a length of at least a portion of the short fibers is substantially smaller than a diameter of the formed tube. For example, in some embodiments, the short fibers may be less than 0.05 mm long. In other embodiments, the short fibers may be between 0.05 and 8 mm long, or more narrowly between 0.1 and 0.4 mm long or 0.3 and 0.4 mm long.

Furthermore, the size and distribution of pores created by erosion of bioceramic particles can also influence the degradation rate and time of the polymer matrix. Smaller particles, such as nanoparticles, create a porous network that exposes a larger volume of polymer matrix to bodily fluid than larger particles, like microparticles. As a result the degradation rate and time of the matrix may be higher when nanoparticles are used rather than microparticles.

Through appropriate selection of the type of material for the particles and the size and shape of the particles, the particles and the device can be designed to have a selected erosion rates and degradation time. For example, the particles can designed erode away in several minutes, hours, days, or a month upon exposure to bodily fluid.

As indicated above, many biodegradable polymers degrade by the mechanism of hydrolysis. The rate of the hydrolysis reaction tends to increase as the pH decreases. Since the degradation products of such polymers as polylactides are acidic, the degradation products have an autocatalytic effect. Therefore, the pH of the degradation products of the bioceramics can also affect the degradation rate of a device. Therefore, bioceramic particles with acidic degradation by-products may further increase the rate of degradation of a matrix polymer.

For example, tricalcium phosphate releases acidic degradation products. Thus, some embodiments may include a composite including a bioceramic having acidic degradation products upon exposure to bodily fluids. The acidic degradation products can increase the degradation rate of the polymer which can decrease the degradation time of the device.

In other embodiments, a composite can have bioceramic particles that have basic degradation products. For example, hydroxyapatite releases basic degradation products. The basic degradation products of the bioceramic particles can reduce the autocatalytic effect of the polymer degradation by neutralizing the acidic degradation products of the polymer degradation. In some embodiments, the basic degradation products of the bioceramic particles can reduce the degradation rate of the polymer. Additionally, bioceramic particles having a basic degradation product may also depress foreign body reaction.

For example, in rapidly eroding implantable medical devices, such as, for example poly(lactide-co-glycolide) which can potentially produce a local pH drop due to the rapid release of acidic degradation products, the use of bioceramic particles having a basic degradation product may buffer the reaction and neutralize the local pH drop.

Furthermore, some semi-crystalline biodegradable polymers have a degradation rate that is slower than desired for certain stent treatments. As a result, the degradation time of a stent made from such polymers can be longer than desired. For example, a stent made from poly(L-lactide) can have a degradation time of between about two and three years. In some treatment situations, a degradation time of less than a year may be desirable, for example, between four and eight months.

As discussed above, the degradation of a hydrolytically degradable polymer follows a sequence including water penetration into the polymer followed by hydrolysis of bonds in the polymer. Thus, the degradation of a polymer can be influenced by its affinity for water and the diffusion rate of water through the polymer. A hydrophobic polymer has a low affinity for water which results in a relatively low water penetration. In addition, the diffusion rate of water through crystalline regions of a polymer is lower than amorphous regions. Thus, as either the affinity of a polymer for water decreases or the crystallinity increases, water penetration and water content of a polymer decreases.

Further embodiments of a biodegradable implantable medical device may be fabricated from a copolymer. In certain embodiments, the copolymer can be a matrix in a bioceramic/polymer composite. The copolymer can include hydrolytically degradable monomers or functional groups that provide desired degradation characteristics. For instance, the copolymer can include functional groups that increase water penetration and water content of the copolymer. In some embodiments, a copolymer can include a primary functional group and at least one additional secondary functional group. In one embodiment, the copolymer may be a random copolymer including the primary functional group and at least one additional secondary functional group.

In an embodiment, the copolymer with at least one secondary functional group can have a higher degradation rate than a homopolymer composed of the primary functional group. A stent fabricated from the copolymer can have a lower degradation time than a stent fabricated from a homopolymer composed of the primary functional group.

In an embodiment, the weight percent of the secondary functional group can be selected or adjusted to obtain a desired degradation rate of the copolymer or degradation time of a stent made from the copolymer. In some exemplary embodiments, the weight percent of the secondary functional group in a copolymer can be at least 1%, 5%, 10%, 15%, 30%, 40%, or, at least 50%. In certain exemplary embodiments, a secondary functional group can be selected and the weight percent of the a secondary functional group can be adjusted so that the degradation time of a stent, with or without dispersed bioceramic particles, can be less than 18 months, 12 months, 8 months, 5 months, 3 months, or more narrowly, less than 1 month.

In some embodiments, the copolymer with at least one secondary functional group can have a lower crystallinity than a homopolymer composed of the primary functional group. It is believed that inclusion of a secondary functional group can perturb the crystalline structure of a polymer including the primary functional group, resulting in a reduced crystallinity. As a result, a stent fabricated from the copolymer has a larger percentage of amorphous regions, which allow greater water penetration. Thus, the degradation rate of the copolymer can be increased and the degradation time of a stent made from the copolymer can be decreased.

In one embodiment, a secondary functional group can be a stereoisomer of the primary functional group. One exemplary embodiment can include a poly(L-lactide-co-DL-lactide) copolymer. DL-lactide can be a secondary functional group that perturbs the crystalline structure of the poly(L-lactide) so that the copolymer has a lower crystallinity than the poly(L-lactide).

In some embodiments, increasing the number of secondary functional groups in the copolymer can result in a decrease in modulus of the copolymer as compared to a homopolymer of the primary functional group. The decrease in modulus can be due to the decrease in crystallinity. The decrease in modulus can reduce the ability of a stent to support a vessel. Thus, the weight percent of the secondary functional group can be adjusted so that the ability of a stent to act as structural support is not substantially reduced. The inclusion of bioceramic particles in the copolymer can partially or completely compensate for the reduction in the modulus of the copolymer.

In other embodiments, the copolymer can include at least one secondary functional group with a greater affinity for water than the primary functional group. The secondary functional group can be less hydrophobic or more hydrophilic than the primary functional group. The decreased hydrophobicity or increased hydrophilicity can increase the concentration of water near bonds prone to hydrolysis, increasing the degradation rate and lowering the degradation time of a stent made from the copolymer.

In certain embodiments, the secondary functional groups can be selected so that segments of the copolymer with a secondary functional group can degrade faster than the primary functional group segments. The difference in degradation rate can be due to the secondary functional groups being more hydrolytically active than the primary functional group. In one embodiment, a secondary functional group can be selected such that a homopolymer including the secondary functional group has a higher degradation rate than a homopolymer including the primary functional group.

In an exemplary embodiment, the copolymer can be poly (L-lactide-co-glycolide). The primary functional group can be L-lactide and the secondary functional group can be glycolide. The weight percent of the glycolide in the copolymer can be at least 1%, 5%, 10%, 15%, 30%, 40%, or, at least 50%. In certain exemplary embodiments, the weight percent of glycolide group can be adjusted so that the degradation time of a stent, with or without dispersed bioceramic particles, can be less than 18 months, 12 months, 8 months, 5 months, or more narrowly, 3 months or less.

Further embodiments of the invention include formation of a bioceramic/polymer composite and fabrication of an implantable medical device therefrom. As indicated above, a composite of a polymer and bioceramic particles can be extruded to form a polymer construct, such as a tube. A stent can then be fabricated from the tube. The composite can be formed in a number of ways. In some embodiments, the composite can be formed by melt blending. In melt blending the bioceramic particles are mixed with a polymer melt. The particles can be mixed with the polymer melt using extrusion or batch processing.

In one embodiment, the bioceramic particles can be combined with a polymer in a powdered or granular form prior to melting of the polymer. The particles and polymer can be mixed using mechanical mixing or stirring such as agitation of the particles and polymer in a container or a mixer. The agitated mixture can then be heated to a temperature above the melt temperature of the polymer in an extruder or using batch processing.

However, a problem with the mechanical mixing or stirring techniques is that the polymer and particles may be separated into separate regions or layers. This is particularly a problem with respect to smaller particles such as nanoparticles. Additionally, obtaining a uniform dispersion by mixing particles with a polymer melt as described, is that particles can agglomerate or form clusters. The mechanical mixing in an extruder or in batch processing can be insufficient to break up the clusters, resulting in a nonuniform mixture of bioceramic particles and polymer. Some embodiments may include forming a composite from a suspension of bioceramic particles and a polymer solution. A composite formed using a suspension may result in a composite having more uniformly dispersed particles than methods formed without using a suspension.

Alternatively, bioceramic particles can be mixed with a polymer by solution blending in which a composite mixture of bioceramic particles and polymer is formed from a suspension of particles in a polymer solution. Certain embodiments of a method of forming an implantable medical device may include forming a suspension including a fluid, a polymer, and bioceramic particles. A "suspension" is a mixture in which particles are suspended or dispersed in a fluid. The fluid can be a solvent for the polymer so that the polymer is dissolved in the fluid. The particles can be mixed with the fluid before or after dissolving the polymer in the fluid.

Various mechanical mixing methods known to those of skill in the art may be used to disperse the bioceramic particles in the suspension. In one embodiment, the suspension can be treated with ultrasound, for example, by an ultrasonic mixer. After formation of a suspension, the polymer and bioceramic particles may then removed from the suspension to form a well dispersed composite mixture. The polymer and bioceramic particles can be removed from the suspension to form the composite mixture in a number of ways. Various embodiments are presented below for forming the composite mixture from the suspension solution.

Some embodiments of forming a composite mixture from the suspension can include combining the suspension with a second fluid that may be a poor solvent for the polymer. At least some of polymer may be allowed to precipitate upon combining the suspension solution with the second fluid. In some embodiments, at least some of the bioceramic particles may precipitate from the suspension with the precipitated polymer to form a composite mixture.

The precipitated composite mixture may then be filtered out of the solvents. The filtered composite mixture can be dried to remove residual solvents. For example, the composite mixture can be dried in a vacuum oven or by blowing heated gas on the mixture.

Exemplary polymers may include, but are not limited to, poly (L-lactic acid), poly (DL-lactic acid), poly (lactide-coglycolide). Representative solvents for such polymers can include toluene and chloroform. Representative poor solvents for these polymers that may be used to precipitate the polymer include methanol, ethanol, isopropanol, and various alkanes such as hexane or heptane.

It is believed that in a suspension including bioceramic nanoparticles, the particles can have strong interactions with polymer chains in solution which can result in particles becoming encapsulated or surrounded by polymer chains. Thus, when the polymer is precipitated from the solution, the interactions of the particles with the polymer can overcome interactions of the particles with the solution so that the particles precipitate with the polymer.

Additionally, it has been observed that the both the degree of precipitation of particles and the degree of dispersion of particles within the precipitated polymer depends upon the amount of polymer dissolved in the solution. The degree of precipitation refers to the amount of particles that precipitate out of the suspension. The degree of dispersion of particles within the precipitated polymer refers to the degree of mixing of the particles with the polymer.

The amount of polymer can be quantified by the weight percent of the polymer in the suspension solution. In addition, the viscosity of the solution is also related to the amount of polymer in the solution. The higher the weight percent of dissolved polymer, the higher is the viscosity of the suspension solution.

For a given concentration of suspended particles, as weight percent of dissolved polymer or viscosity is reduced, the degree of precipitation of particles is reduced. This is likely due to the reduced interaction of the particles with the polymer chains. Thus, at lower weight percent of polymer or viscosity, the amount of particles precipitating can be relatively low.

Additionally, for a given concentration of suspended particles, as the weight percent of polymer or viscosity of the solution is increased beyond an observed range, the degree of dispersion of particles in the precipitated polymer tends to decrease. It is believed that at higher weight percent of polymer or higher viscosity, the interactions between polymer chains reduce the interaction of particles with polymer chains that cause particles to precipitate. For example, particles may be unable to move freely among the polymer chains.

A given suspension can have a particular combination of type of particles, particle concentration, and solvent. For this given suspension, the polymer weight percent or viscosity that can be varied to obtain both a desired degree of precipitation of particles and degree of dispersion of particles in the precipitated polymer. Thus, there may be a range of polymer weight percent or viscosity that can result in a desired degree of precipitation of particles and degree of dispersion of particles in precipitated polymer.

Additionally, the manner of combining the suspension with the poor solvent can also affect the degree of precipitation and degree of dispersion. For example, depositing a fine mist of small droplets into a poor solvent can more readily result in a desired degree of precipitation and degree of dispersion. Thus, the manner of combining the suspension with the poor solvent can influence the range of polymer weight percent or viscosity that results in a desired degree of precipitation and degree of dispersion.

Further embodiments of forming a composite mixture can include evaporating at least some of the solvent in the suspension solution. As the solvent evaporates, at least some of the polymer may separate or precipitate from the suspension, and thus be removed from the suspension. In some embodiments, at least some of the bioceramic particles may separate from or precipitate from the suspension solution along with the polymer upon evaporation the solvent to form the composite mixture. In an embodiment, all or substantially all of the solvent can be evaporated from the suspension, leaving a composite mixture. The evaporation of the solvent can be facilitated by increasing the temperature of the suspension, for example, by applying heat to the suspension. Additionally or alternatively, the evaporation of the solvent can be facilitated by decreasing the pressure of the above the suspension.

In certain embodiments, the evaporation of the solvent can be facilitated by subjecting the suspension to spray drying which involves atomizing the suspension or forming a plurality of fine droplets of suspension. For example, the suspension can be forced through an atomizing device such as a spray nozzle to form an atomized stream of droplets. The increase in surface to volume ratio of the atomized suspension increases the rate of the evaporation of the solvent. Additionally, the evaporation of the solvent from the droplets can be further enhanced by increasing the temperature of the droplets. In one embodiment, the temperature can be increased by spraying the droplets into a stream of heated gas. The temperature can also be controlled by spraying the droplets within a heated chamber. In additional embodiments, the evaporation of the solvent can be further be facilitated by decreasing the pressure of the droplets. For example, a pump in communication with the chamber can reduce the pressure in the chamber below the vapor pressure of the solvent. Additionally, the pressure can be decreased by subjecting the suspension to flash evaporation in which the suspension undergoes a reduction in pressure by passing it through a throttling valve or other throttling device.

As the solvent in the droplets evaporates, at least some of the polymer separates from the suspension. Additionally, at least some of the bioceramic particles may be separated along with the polymer upon spraying to form the composite mixture. In an embodiment, process parameters can be adjusted so that all or substantially all of the solvent evaporates and the composite mixture can be recovered. Process parameters include the size of the droplets, the temperature and pressure in a chamber, the temperature of a heated gas stream, throttling pressure, and the distance between a spray nozzle and a recovery receptacle.

FIG. 4A-C depict an exemplary system and process for forming a composite mixture. FIG. 4A depicts a suspension 405 which is formed in a container 410. Suspension 405 includes a polymer solution 415 and bioceramic particles 420 mixed or suspended in solution 415.

In one embodiment, the suspension can be formed by mixing a solution of solvent and surfactant with bioceramic particles 420 by vigorous stirring with a mechanical stirrer 440. A polymer is gradually added to the suspension during the stirring and stirring is continued at least until all of the polymer is dissolved. In some embodiments, ultrasonic mixing is used to further disperse all the bioceramic particles uniformly into the polymer matrix.

FIG. 4B depicts a spray-drying apparatus 400 for separating the polymer and particles 420 from solution 415. System 400 includes an atomizing device or spray nozzle 445. Suspension 405 is fed into nozzle 445, as shown by an arrow 450, along with an air stream 455. Nozzle 445 produces a spray plume 470 including a plurality of droplets. FIG. 4C shows an expanded view of a droplet 460 from spray plume 470. As the droplets in spray plume 470 fall away from nozzle 445 as shown by an arrow 480, the solvent in the droplets evaporates. A heated gas nozzle blows heated gas 481 onto spray plume 470 to facilitate evaporation of the solvent in the droplets. System 400 can be enclosed in a chamber (not shown) so that the temperature and pressure can be adjusted to control the rate of evaporation.

All or substantially all of the solvent evaporates from the droplets leaving particles 482 of composite mixture of polymer and bioceramic particles 420. Particles 482 of the composite mixture 470 are collected in a container 485. The composite mixture formed can be removed for further processing to form an implantable medical device.

Further embodiments of forming a composite mixture from the suspension can include removal of the solvent from the suspension by forming a two phase liquid system of the suspension solution and another fluid. In some embodiments, the method may include forming a mixture of the suspension solution and a second fluid that is a poor solvent for the polymer and is immiscible with the solvent so that a suspension solution phase and a second fluid phase is formed. In one embodiment, the solvent is an organic fluid and the second fluid is aqueous. At least some of polymer may precipitate upon combining the suspension solution with the second fluid due to leaching of the solvent into the second fluid phase. In some embodiments, at least some of the bioceramic particles may precipitate from the suspension with the precipitated polymer to form a composite mixture. The precipitated composite mixture can be then be separated from the liquid phases through filtering or evaporation of the liquid phases. For example, evaporation can be facilitated by atomizing a two liquid phase system in a similar manner as the single liquid phase system described above.

In certain embodiments, the leaching of the solvent into the second fluid phase can be facilitated by forming an emulsion of the solvent within the second fluid phase. An "emulsion" is a mixture of two immiscible substances in which one substance (the dispersed phase) is dispersed in the other (the continuous phase). Thus, the suspension fluid phase may be dispersed within the second fluid phase. An emulsion can include a plurality of suspension fluid phase droplets dispersed within a second fluid phase. Such an emulsion can be formed using vigorous high shear mixing devices that are known to one of skill in the art.

Figure 5A:
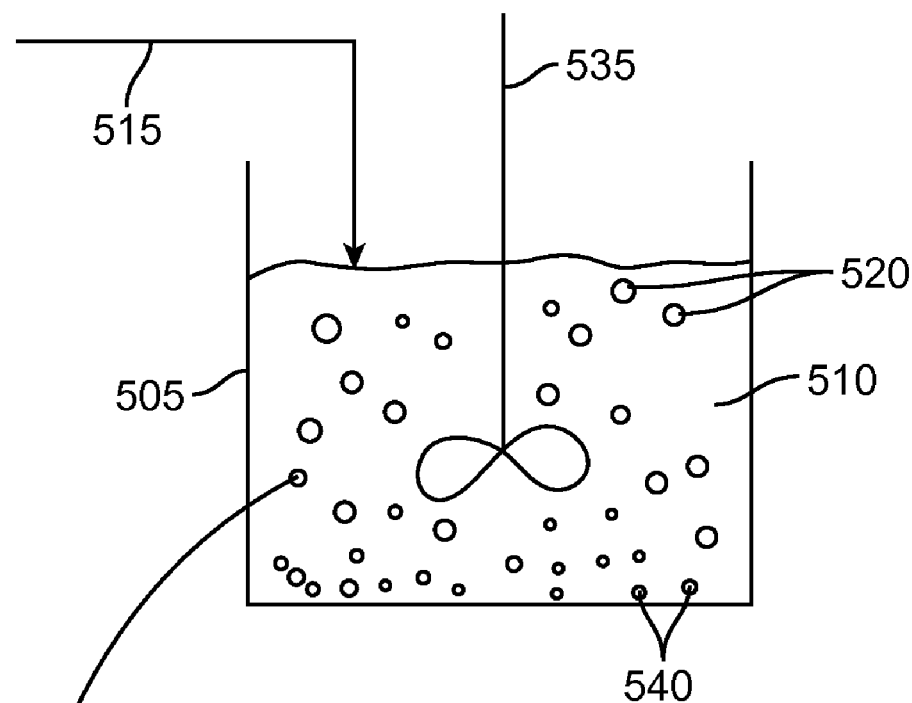
FIG. 5A-B depicts an exemplary system and process for forming a composite mixture
Figure 5B:
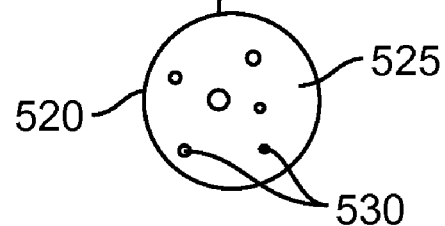

FIG. 5A-B depict an exemplary system 500 for forming a composite mixture from a two phase liquid system of the suspension solution and an aqueous fluid. A suspension solution 515 is added to a container 505 having an aqueous fluid or phase 510. Suspension solution 515 includes a polymer dissolved in an organic solvent with dispersed bioceramic particles. The added suspension solution 515 can form a plurality of droplets of an organic phase 520 within aqueous phase 510. In FIG. 5B, an expanded view of organic phase 520 shows bioceramic particles 530 dispersed within an organic solvent 525. The plurality of droplets of organic phase 520 can be formed by high shear mixing by a mixing apparatus 535. As organic solvent 525 leaches out of organic phase 520 into aqueous phase 510, polymer and bioceramic particles separate from the suspension phase to form particles 540 of composite mixture. Particles 540 can be separated through filtration.

Figure 6A:
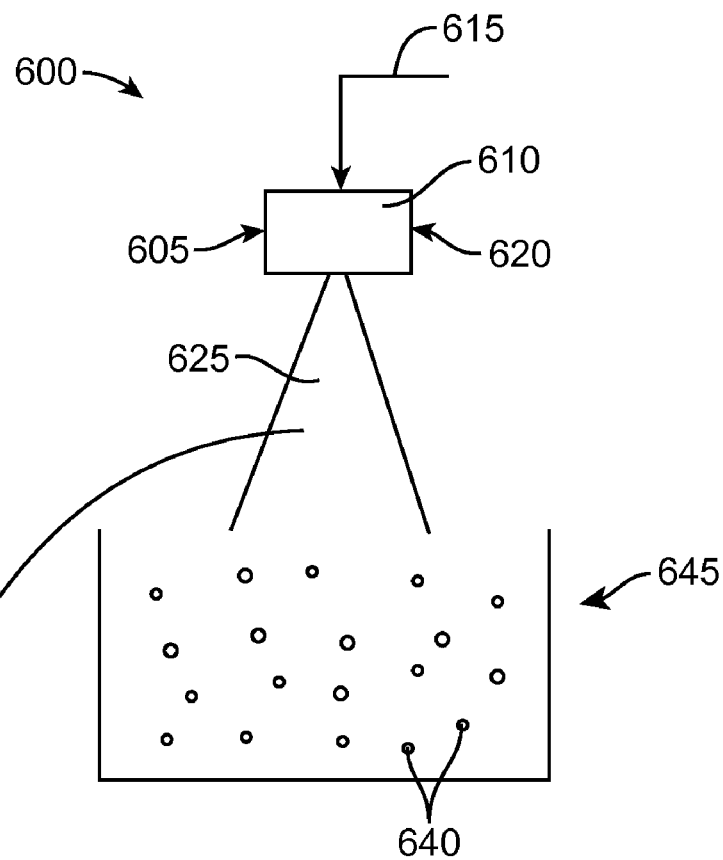
FIG. 6A-B depicts an exemplary system and process for forming a composite mixture
Figure 6B:
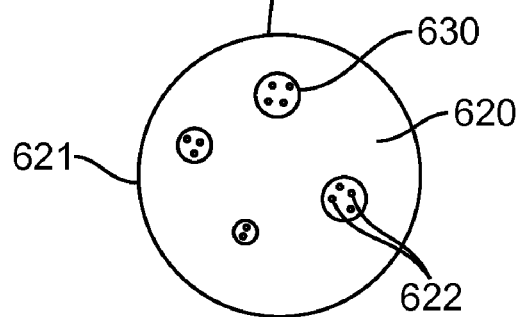

FIG. 6A-B depict an exemplary system and process for forming a composite mixture. FIG. 6A depicts a solvent evaporating apparatus 600. A suspension solution 605, including dissolved polymer and bioceramic particles mixed or suspended in a solution, is added to solvent evaporating system 600. The suspension solution can include a surfactant that facilitates the dispersion of the particles and reduces or prevents agglomeration of the particles. System 600 includes an atomizing device or spray nozzle 610. Suspension solution 605 is fed into nozzle 610, along with an air stream 615. Suspension solution 605 is mixed with an aqueous fluid 620 which is also fed into nozzle 610. Nozzle 610 produces a spray plume 625 including a plurality of droplets that includes an organic phase 630 within an aqueous phase 620, as shown by droplet 621 organic phase 630 includes bioceramic particles 622 in FIG. 6B As organic solvent leaches out of organic phase 630 into aqueous phase 620, polymer and bioceramic particles separate from the suspension solution to form particles 640 of composite mixture. All or substantially all of the organic and aqueous phase evaporates from the droplets leaving particles 640 of composite mixture including polymer and bioceramic particles. Particles of the composite mixture 640 are collected in a container 645. The composite mixture formed can be removed for further processing to form an implantable medical device.

Further embodiments of the method include conveying the composite mixture into an extruder. The composite mixture may be extruded at a temperature above the melting temperature of the polymer and less than the melting temperature of the bioceramic particles. In some embodiments, the dried composite mixture may be broken into small pieces by, for example, chopping or grinding. Extruding smaller pieces of the composite mixture may lead to a more uniform distribution of the nanoparticles during the extrusion process.

The extruded composite mixture may then be formed into a polymer construct, such as a tube or sheet which can be rolled or bonded to form a tube. A medical device may then be fabricated from the construct. For example, a stent can be fabricated from a tube by laser machining a pattern in to the tube.

In another embodiment, a polymer construct may be formed from the composite mixture using an injection molding apparatus.

Preparation of a desired amount of precipitated composite mixture may require a large amount of solvent and precipitant. Therefore, in some embodiments, it may be advantageous to melt blend precipitated composite mixture with an amount of polymer in an extruder or in a batch process. The polymer can be the same or a different polymer of the precipitated composite mixture. For example, a relatively small amount of precipitated composite mixture that has a weight percent of bioceramic particles higher than is desired can be prepared. The precipitated composite mixture may be melt blended with an amount of biodegradable polymer to form a composite mixture than has a desired weight percent of bioceramic particles.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly (caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The examples and experimental data set forth below are for illustrative purposes only and are in no way meant to limit the invention. The following examples are given to aid in understanding the invention, but it is to be understood that the invention is not limited to the particular materials or procedures of examples. The bioceramic particles used in the examples were hydroxyapatite (HAP) and calcium sulfate. The polymers used in the Examples were poly (L-lactic acid) (PLLA), poly (DL-lactic acid) (PDLLA), and poly (lactic acid co-glycolide) (PLGA).

EXAMPLE 1

Prophetic Example of Solution Blending of Polymer and Bioceramic Particles

Step 1: Add bioceramic particles into suitable solvent, such as chloroform, acetone, etc. and stir to form a bioceramic particle suspension solution.

Step 2: Slowly add a polymer such as PLLA, PDLLA, PGLA into suspension solution and stir until polymer dissolves completely. In this step, the solution may still have a relatively low viscosity. However, the bioceramic particles should be well dispersed while stirring.

Step 3: Slowly add the polymer into solution again to gradually increase solution viscosity. Repeat this step as needed until the polymer is completely dissolved and reasonable solution viscosity is developed.

Step 4: Apply ultrasonic mixing to suspension solution for 15-30 min to further disperse all the bioceramic particles uniformly into the PLLA solution.

Step 5: An atomized device is used to flash solvent out or evaporate solvent out at high pressure and temperature above solvent vapor pressure.

Step 6: Collect the separated, well-dispersed bioceramic particles/polymer composite mixture.

EXAMPLE 2

Prophetic Example of Solution Blending of Polymer and Bioceramic Particles

Step 1: Add bioceramic particles into suitable solvent, such as chloroform, acetone, etc. and stir to form a bioceramic particle suspension solution.

Step 2: Slowly add a polymer such as PLLA, PDLLA, PGLA into suspension solution and stir until polymer dissolves completely. In this step, the solution may still have a relatively low viscosity. However, the bioceramic particles should be well dispersed while stirring.

Step 3: Slowly add the polymer into solution again to gradually increase solution viscosity. Repeat this step as needed until the polymer is completely dissolved and reasonable solution viscosity is developed.

Step 4: Apply ultrasonic mixing to suspension solution for 15-30 min to further disperse all the bioceramic particles uniformly into the PLLA solution.

Step 5: Slowly combine or emulsify organic phase with aqueous phase.

Step 6: Additional aqueous phase material is added to leach out solvent.

Step 7. Collect the precipitated bioceramic particles/polymer composite mixture.

EXAMPLE 3

Solution Blending of PLLA/HAP Composite (100:1 wt/wt)

Step 1: Added 50 mg HAP particles into 300 mL of chloroform and stirred for 10-30 minutes to form bioceramic particle suspension solution.

Step 2: Slowly added 5 g PLLA into suspension solution and stirred about 8 hours to dissolve all polymer.

Step 3: Applied ultrasonic mixing to suspension solution for 15-30 min to further disperse HAP particles into PLLA solution.

Step 4: Added suspension solution to 1 L methanol to precipitate polymer and particles.

Step 5: Filtered the precipitate and dried about 8 hours in vacuum oven at 60° C. End product is PLLA/HAP composite. Composites were also made with 2 wt % and 5 wt % HAP.

Mechanical Properties and Morphology of PLLA/HAP Composite (100:1 wt/wt)

Tensile testing of the composite samples and a pure PLLA were performed using an Instron tensile tester obtained from Instron in Canton, Mass. Test samples were prepared by hot pressing the PLLA/HAP composites and pure polymer to a thin film at 193° C. for 30 seconds. Testing bars were cut from the thin film and tested. The peak stress at break, the strain at break, and the Young's modulus were measured. The draw rate was about 0.5 in/min.

Figure 7:
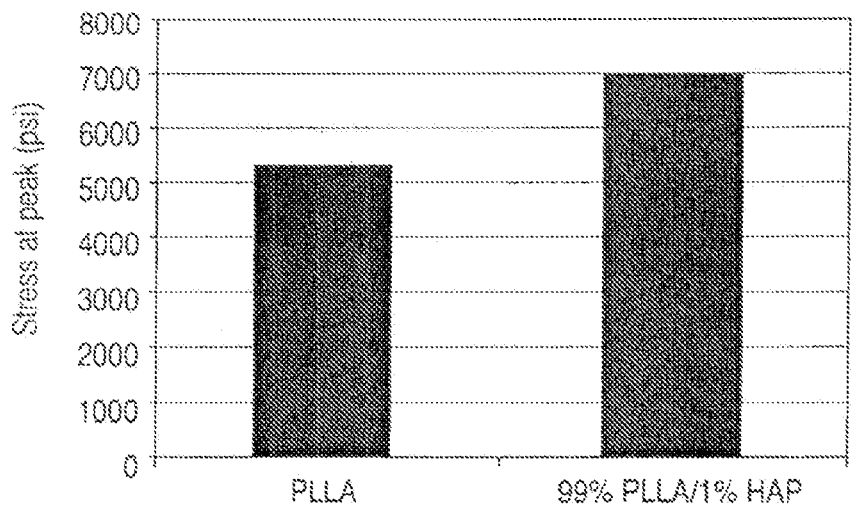
FIG. 7 is a graph depicting the peak stress for PLLA and PLLA/HAP composites.
Figure 8:
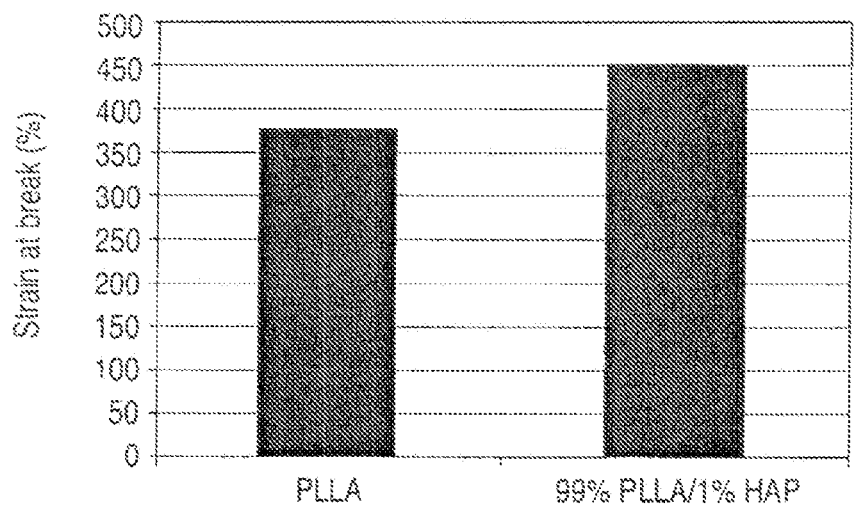
FIG. 8 is a graph depicting the break strain for PLLA and PLLA/HAP composites.
Figure 9:
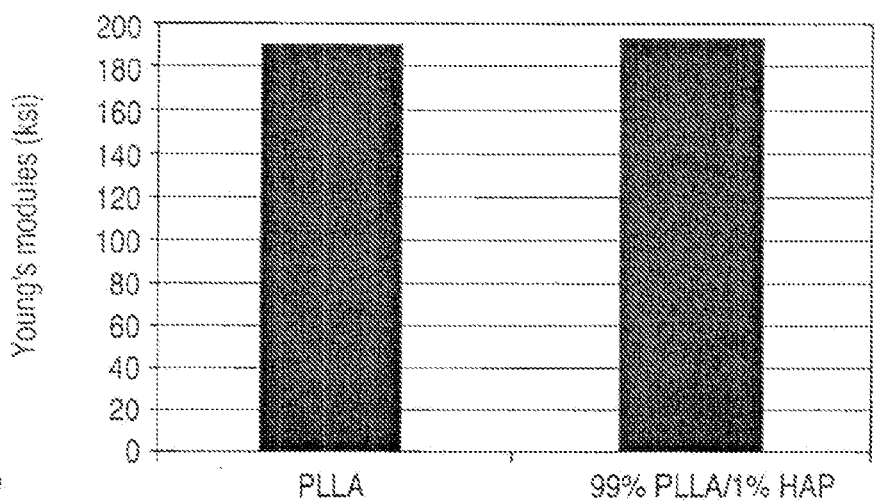
FIG. 9 is a graph depicting Young's modulus for PLLA and PLLA/HAP composite stent in compression testing.

FIGS. 7-9 illustrate tensile testing results for pure PLLA and PLLA/HAP composites with 1 wt % HAP. FIG. 4 depicts the peak stress for the two samples. PLLA/HAP composites have a higher peak stress than the pure PLLA. FIG. 5 depicts the % strain at break for the two samples. The 1 wt % composite had a higher % strain at break than the pure PLLA. FIG. 6 depicts Young's modulus for the two samples. The 1 wt % samples had a higher Young's modulus than the pure PLLA.

EXAMPLE 4

Solution Blending of PLLA/HAP Composite (2:1 wt/wt) as HAP Intermedium Mixture

Step 1: Added 25 g HAP particles to 3 L chloroform and stirred for 10-30 minutes to form bioceramic particle suspension solution.

Step 2: Slowly added 50 g PLLA into suspension solution and stirred about 8 hours to dissolve all polymer.

Step 3: Applied ultrasonic mixing for 15-30 min to further disperse HAP particles into PLLA solution.

Step 4: Added suspension solution to 9 L methanol to precipitate particles and polymer.

Step 5: Filtered the precipitate and dried about 8 hours in vacuum oven at 60° C. End product is PLLA/HAP composite.

Extrusion of Precipitated PLLA/HAP (2:1 wt/wt) with PLLA

Step 1: Broke 2:1 wt/wt composite into small pieces

Step 2: Mixed 24 g of broken up composite and 376 g PLLA.

Step 3: Extruded mixture at 216° C.

EXAMPLE 5

Extrusion of Precipitated PLGA/HAP (2:1 wt/wt) with PLGA

Step 1: Broke PLGA/HAP composite into small pieces

Step 2: Mixed 12 g broken up PLGA/HAP composite and 396 g PLGA.

Step 3: Extruded mixture at 216° C.

EXAMPLE 6

As discussed above, to further improve mechanical properties of a bioceramic and polymer composite, the interfacial adhesion can be enhanced. The adhesion between bioceramic particles and a biodegradable polymer can be improved by coating at least a portion of the surfaces of the bioceramic particles with an adhesion promoter such as 3-aminopropyltrimethoxysilane and 3-aminopropyltriethoxysilane.

Example of the Modification of HAP:

Step 1: Added 100 ml distillated water to 1900 ml Ethanol and stirred for 15-30 min.

Step 2: Added 20 g 3-aminopropyltrimethoxysilane to water-ethanol mixture and stirred for 1 h.

Step 3: Added 20 g HAP and stirred for 2 h.

Step 4: Centrifuged the modified HAP from solution.

Step 5: Dried HAP about 8 hours in vacuum oven.

EXAMPLE 7

A stent was fabricated from a PLGA/nanoparticle composite tubing. Prior to cutting a stent pattern, the tubing was expanded at 109° C. in a blow molder to increase radial strength. A stent pattern was cut in the expanded tubing using an ultra-fast pulse laser. The stent was crimped at 30° C. After crimping, the stent was cold sterilized.

EXAMPLE 8

The mechanical properties of a stent fabricated from a PLGA/nanoparticle HAP composite were tested on an Instron compression tester. The recoil of stents was recorded after inflation and deflation of stent.

Figure 10:
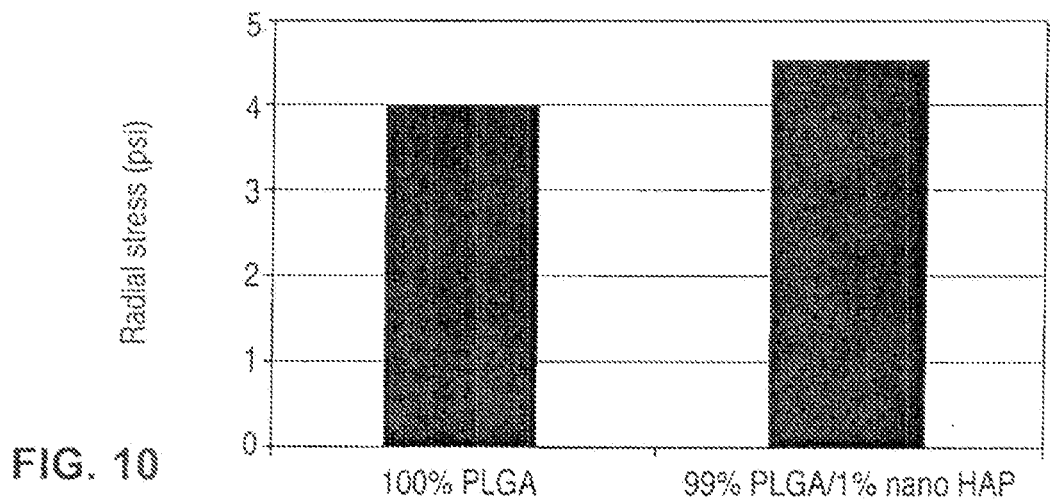
FIG. 10 is a graph depicting the radial stress for PLGA and PLGA/HAP composite stent in compression testing.
Figure 11:
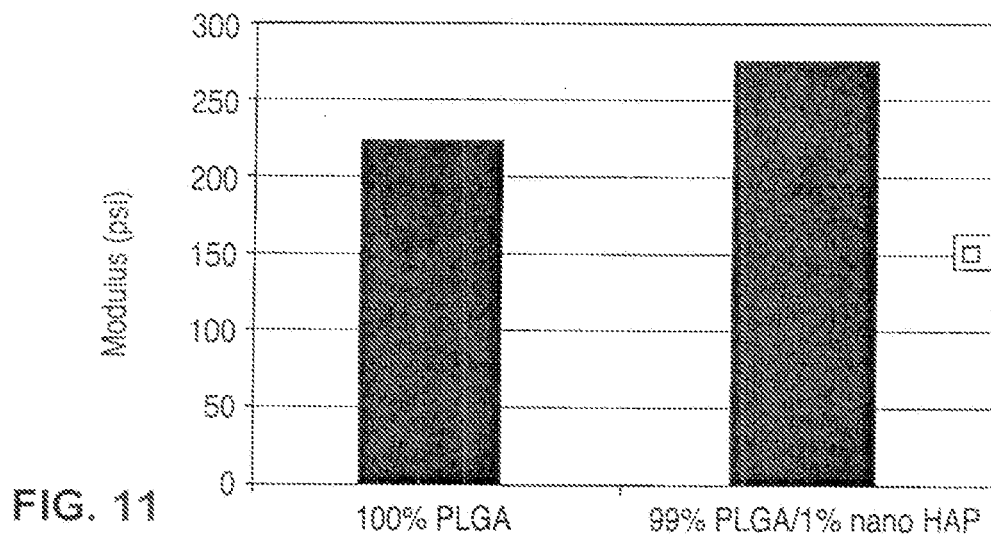
FIG. 11 is a graph depicting the compression modulus for PLGA and PLGA/HAP composite stent in compression testing.

FIGS. 10 and 11 illustrate compression testing results for PLGA/HAP stent (100:1 wt/wt). The compression testing results for 100% PLGA is also included for comparison. FIG. 7 shows that the average radial strength of PLGA/HAP stent is about 11% higher than that of the 100% PLGA stent. FIG. 8 shows that the compression modulus of PLGA/nano HAP stent increased by about 23% over the 100% PLGA stent.

Figure 12:
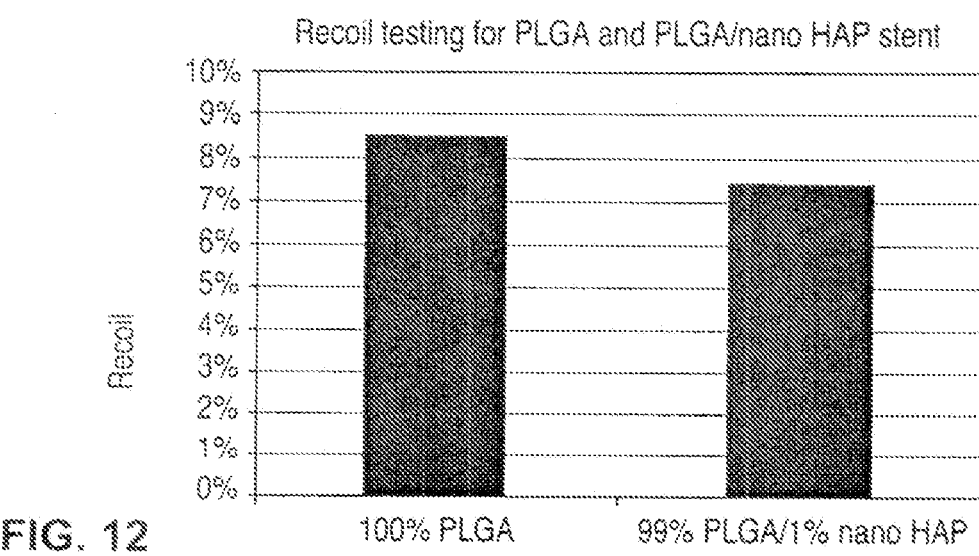
FIG. 12 is a graph depicting recoil testing of PLGA and PLGA/HAP composite stent.
Figure 13A:
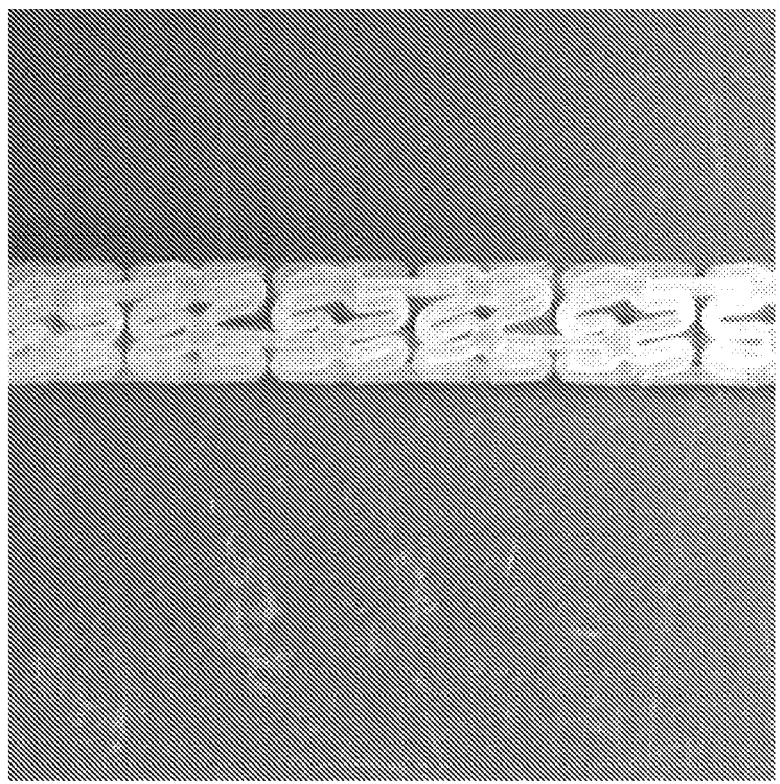
FIGS. 13A-D depict photographic images of a PLGA/calcium sulfate composite stent with a weight ratio of PLGA/calcium sulfate of 100:1 at zero time point.
Figure 13B:
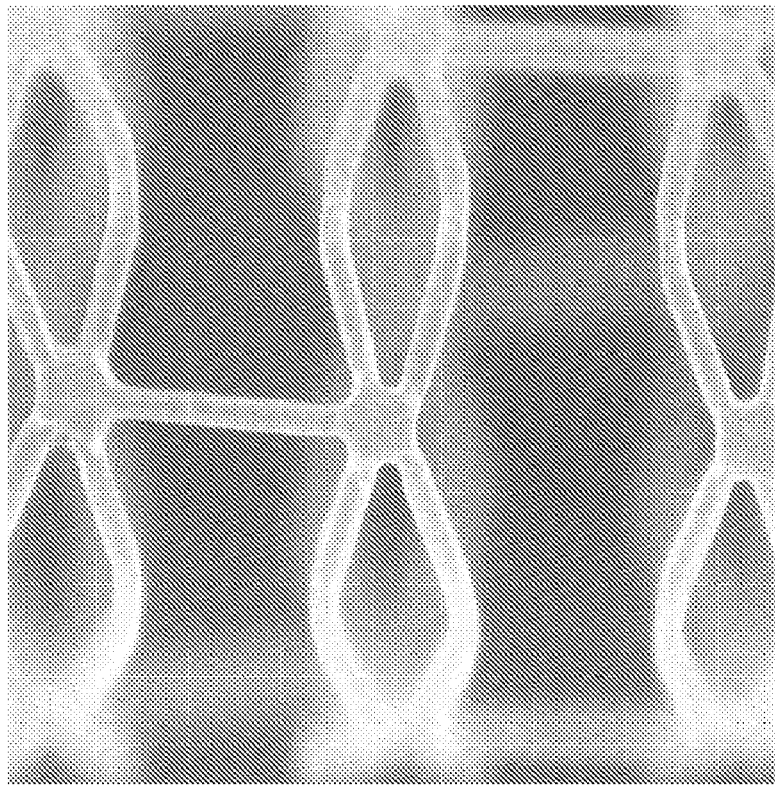
Figure 13C:
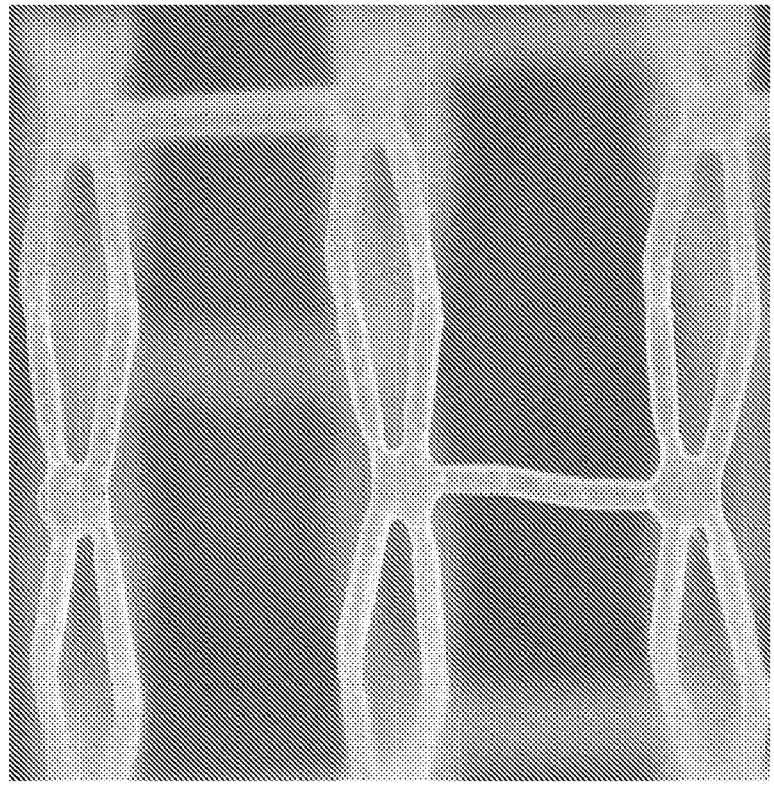
Figure 13D:
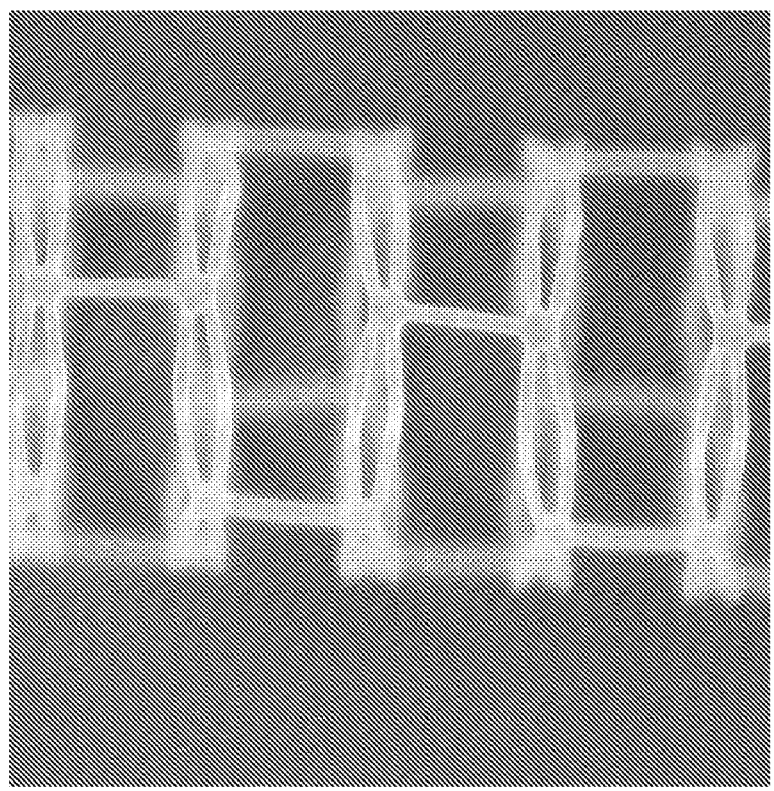
Figure 14A:
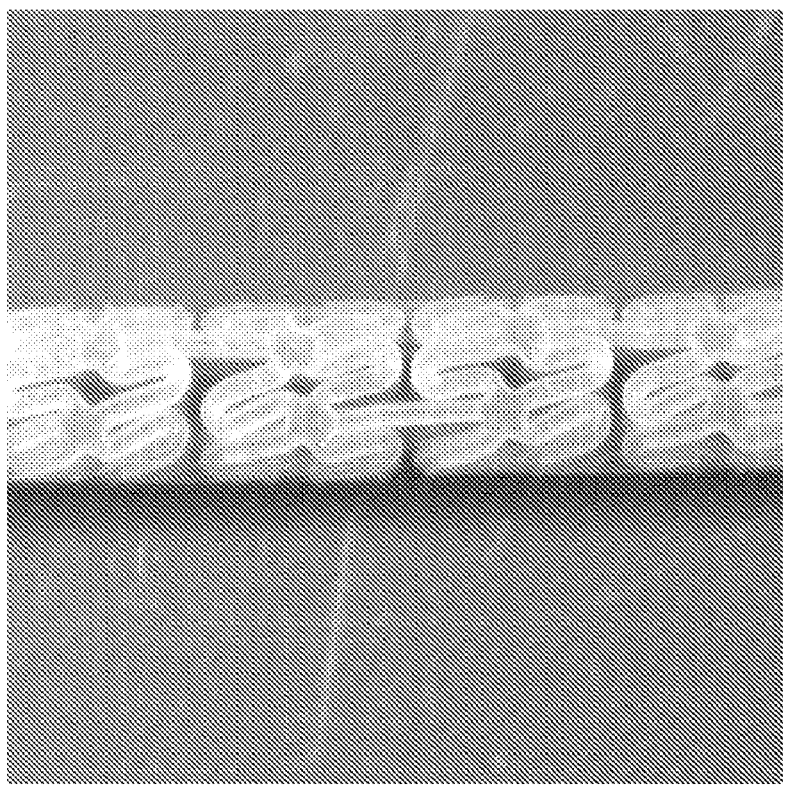
FIGS. 14A-D depict photographic images of a PLGA/calcium sulfate composite stent with a weight ratio of PLGA/calcium sulfate of 100:1 at 16 hours of accelerated aging.
Figure 14B:
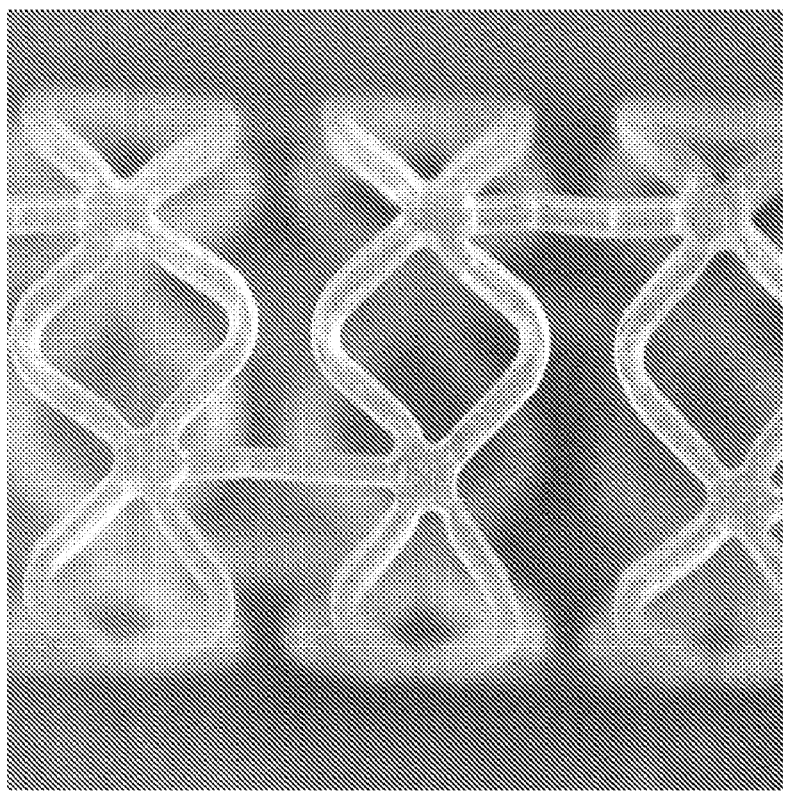
Figure 14C:
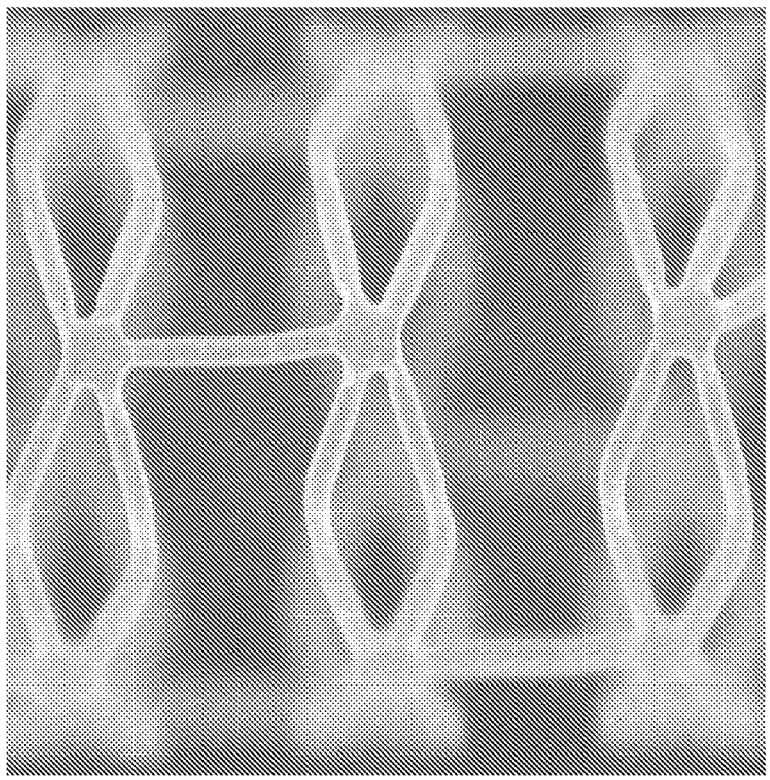
Figure 14D:
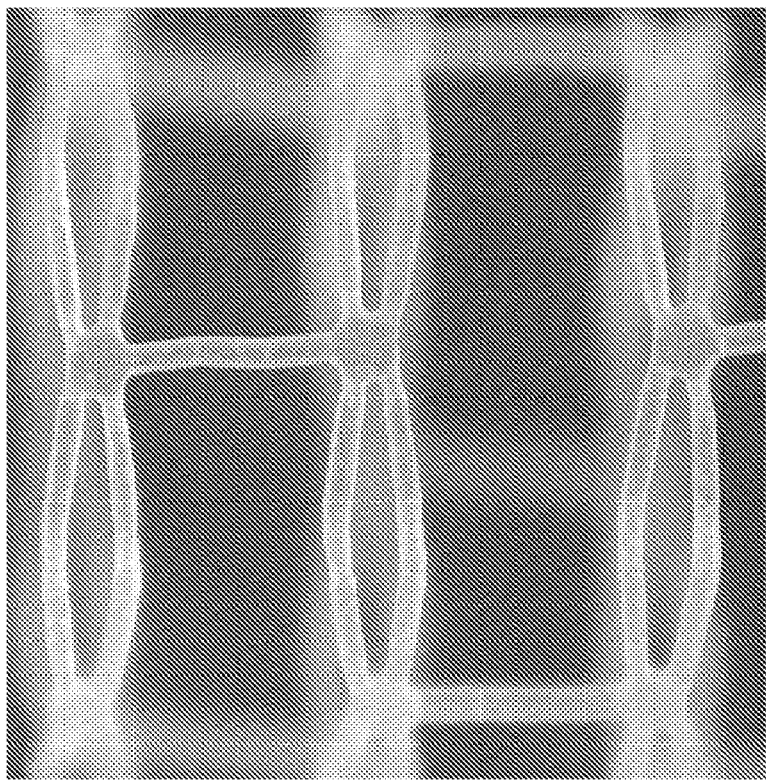

FIG. 12 shows the recoil of PLGA/nano HAP stent is about 15% less than the PLGA stent.

EXAMPLE 9

Stents were fabricated from a bioceramic/polymer composite with a matrix of PLGA copolymer. Calcium sulfate nanoparticles, which were pretreated by PEG-PPG-PEG surface modifier, were mixed with the copolymer matrix. PEG refers to polyethylene glycol and PPG refers to polypropylene glycol. The copolymer had 85 wt % L-lactide and 15 wt % GA. The composite was fabricated according to methods described herein. The stents were fabricated from tubes made from the composite and the tubes was radially expanded. The expanded tubes were laser cut to form stents.

Stents were fabricated and tested having a ratio of copolymer to particles of 100:1 by weight. Five stent samples were used for each testing (compression, recoil or expansion testing). at a zero time point (after fabrication) and after 16 hours of accelerated aging. Accelerated aging refers to aging at 40° C.

The zero time point samples were subjected to compression testing. Compression tests were performed with an Instron testing machine obtained from Instron in Canton, Mass. A stent sample was placed between two flat plates. The plates were adjusted so that the distance between the plates was the diameter of the stent in an uncompressed state. The plates were then adjusted to compress the stent by 10%, 15%, 25%, and 50% of the uncompressed plate distance. A resistance force, the amount force in units of Newtons/mm that was necessary to keep the stent at each compression distance, was measured. The resistance force corresponds to a measure of the radial strength (Rs). The modulus was also measured. Table 1 provides the compression test results for the 100:1 samples at zero time point. The Rs and modulus correspond to 50% compression.

TABLE 1

Compression test results for 100:1 samples at zero time point.

| Stent # | Rs (psi) | Modulus (psi) |
|---|---|---|
| 1 | 5.867 | 365.5 |
| 2 | 5.443 | 291.5 |
| 3 | 6.027 | 316.9 |
| 4 | 5.879 | 324.2 |
| 5 | 5.539 | 310.1 |
| Avg | 5.751 | 321.6 |
| Std dev | 0.248 | 27.360 |

The stent samples were subjected to recoil testing at both time points for each bioceramic composition. Each stent sample was deployed inside a length of Tecoflex elastic tubing. Tecoflex tubing can be obtained from Noveon, Inc., Cleveland, Ohio. The inside diameter (ID) of the Tecoflex tubing was 0.118 in and the outside diameter (OD) was 0.134 in. The ID of the sheath to hold the stent after crimping was 0.053 in. The stents were deployed to an outer diameter of 3.0 mm by inflating the balloon. The balloon was deflated, allowing the stent to recoil. The diameter of the recoiled stent was then measured.

The percent recoil was calculated from:

% Recoil=(Inflated Diameter−Deflated Diameter)/ Inflated Diameter×100%

The Inflated Diameter is the diameter of a deployed stent prior to deflating the balloon and the Deflated Diameter is the diameter of the recoiled stent. The deployment of the stent also results in an increase in length of the stent. The percent change in length was calculated from:

% Length change=(Crimped length−Deployed length)/Crimped length×100%

Table 2 provides the results of the recoil test for the five 100:1 stent samples at zero time point. As shown in Table 1, the outside diameter (OD) of the stent when the balloon was inflated and deflated was measured at a proximal end, a middle, and distal end of the stent. ODwt refers to the outside diameter with tecoflex tubing and ODS refers to the outside diameter with stent only. The % Total Recoil given is the average of the recoil calculated at each point along the length of the stent.

TABLE 2

Recoil test results for 100:1 stent samples at zero time point.

| | Crimp | | | Inflated @ 8 atm | | | | Deflated Dimensions | | | | | |
|---|---|---|---|---|---|---|---|---|---|---|---|---|---|
| Stent # | Tecoflex DWT Prox | Tecoflex DWT Dist | Stent L (mm) | Stent L (mm) | Prox OD (mm) | Mid OD (mm) | Distal OD (mm) | Stent L (mm) | Prox OD (mm) | Mid OD (mm) | Distal OD (mm) | % Total Recoil | % Length Change |
| 1 | 0.375 | 0.370 | 12.796 | 12.384 | 3.690 | 3.774 | 3.802 | 12.392 | 3.448 | 3.504 | 3.529 | 7.7% | 3.2% |
| 2 | 0.368 | 0.378 | 12.833 | 12.529 | 3.792 | 3.785 | 3.811 | 12.450 | 3.541 | 3.487 | 3.496 | 8.4% | 3.0% |
| 3 | 0.368 | 0.374 | 12.817 | 12.553 | 3.835 | 3.886 | 3.871 | 12.720 | 3.618 | 3.561 | 3.519 | 8.5% | 0.8% |
| 4 | 0.375 | 0.370 | 12.863 | 12.492 | 3.792 | 3.806 | 3.871 | 12.774 | 3.653 | 3.673 | 3.644 | 4.8% | 0.7% |
| 5 | 0.365 | 0.370 | 12.793 | 12.421 | 3.803 | 3.815 | 3.856 | 12.407 | 3.579 | 3.576 | 3.640 | 6.5% | 3.0% |
| | | | | | ODwT | 3.813 | | | | 3.565 | AVG | 7.2% | 2.1% |
| | | | | | ODS | 3.441 | | | | 3.193 | Std Dev | 1.6% | 1.3% |

The stents were subject to expansion testing at both time points. Each stent sample was deployed to an outer diameter of first 3.0 mm, then 3.5 mm, and then 4.0 mm. The number of cracks in the stents were counted at each deployment diameter.

Table 3 provides the number of cracks observed in the 100:1 stent samples at zero time point when deployed at a diameter of 3.5 mm. The columns refer to the size of the cracks: "Micro" refers to micro-sized cracks, "<25%" refers to cracks less than 25% of the strut width, "<50%" refers to cracks less than 50% of the strut width, and ">50%" refers to cracks greater than 50% of the strut width. "A" refers to the "v-shaped" region or bending region of struts and "B" refers to a spider region at the intersection of 5 struts. The regions can be seen in FIGS. 13A-D. No broken struts were observed at either 3.5 mm or 4.0 mm deployment diameters. FIGS. 13A-D depict photographic images of the 100:1 stent sample 1 at zero time point before expansion, expanded to 3.5 mm, after recoil, and after expansion to 4.0 mm, respectively.

TABLE 3

Number of cracks observed at 3.5 mm deployment for 100:1 stent samples at zero time point.
Stents Deployed to 3.5 mm

| Stent # | Micro | <25% | <50% | >50% |
|---|---|---|---|---|
| 1 | | | | |
| A | | 4 | 2 | |
| B | | | | |

TABLE 3-continued

Number of cracks observed at 3.5 mm deployment for 100:1 stent samples at zero time point.
Stents Deployed to 3.5 mm

| Stent # | Micro | <25% | <50% | >50% |
|---|---|---|---|---|
| 2 | | | | |
| A | 2 | | | |
| B | | | | |
| 3 | | | | |
| A | 4 | | | |
| B | | | | |
| 4 | | | | |
| A | | | | |
| B | | | | |
| 5 | | | | |
| A | 1 | | | |
| B | | | | |

Test Results for 100:1 Stent Samples at 16 Hours of Accelerated Acing

Table 4 provides the results of the recoil test for the 100:1 stent samples at 16 hours of accelerated aging. Tables 5A-B provide the number of cracks observed in the 100:1 stent samples at 16 hours of accelerated aging when deployed at a diameter of 3.5 mm and 4.0 mm, respectively. No broken struts were observed at either deployment diameter. FIGS. 14A-D depict photographic images of the 100:1 stent sample 1 at 16 hours of accelerated aging before expansion, expanded to 3.5 mm, after recoil, and after expansion to 4.0 mm, respectively.

TABLE 4

Recoil test results for 100:1 stent samples at 16 hours of accelerated aging.

| | Crimp Dimensions | | | Inflated @ 8 atm Dimensions | | | | Deflated Dimensions | | | | | |
|---|---|---|---|---|---|---|---|---|---|---|---|---|---|
| Stent # | Tecoflex DWT Prox | Tecoflex DWT Dist | Stent L (mm) | Stent L (mm) | Prox OD (mm) | Mid OD (mm) | Distal OD (mm) | Stent L (mm) | Prox OD (mm) | Mid OD (mm) | Distal OD (mm) | % Total Recoil | % Length Change |
| 1 | 0.372 | 0.377 | 12.683 | 12.133 | 3.900 | 3.834 | 3.836 | 12.311 | 3.508 | 3.520 | 3.522 | 9.8% | 2.9% |
| 2 | 0.380 | 0.383 | 12.830 | 12.306 | 3.870 | 3.809 | 3.780 | 12.380 | 3.623 | 3.546 | 3.584 | 6.8% | 3.5% |
| 3 | 0.374 | 0.372 | 12.924 | 12.574 | 3.845 | 3.804 | 3.783 | 12.620 | 3.477 | 3.448 | 3.422 | 10.5% | 2.4% |
| 4 | 0.373 | 0.375 | 12.806 | 12.411 | 3.933 | 3.874 | 3.881 | 12.486 | 3.526 | 3.508 | 3.508 | 10.8% | 2.5% |
| 5 | 0.381 | 0.382 | 12.745 | 12.358 | 3.853 | 3.799 | 3.809 | 12.570 | 3.482 | 3.489 | 3.471 | 9.9% | 1.4% |
| | | | | | | ODwT | 3.841 | | | 3.509 | AVG | 9.6% | 2.5% |
| | | | | | | ODS | 3.464 | | | 3.132 | Std Dev | 1.6% | 0.8% |

TABLE 5A

Number of cracks observed for 100:1 stent samples at 16 hours of accelerated aging deployed at 3.5 mm.
Stents Deployed to 3.5 mm

| Stent # | Micro | <25% | <50% | >50% |
|---|---|---|---|---|
| 1 | | | | |
| A | 2 | 1 | | |
| B | 1 | | | |
| 2 | | | | |
| A | | | | |
| B | | | | |
| 3 | | | | |
| A | 2 | 1 | | |
| B | | | | |

TABLE 5A-continued

Number of cracks observed for 100:1 stent samples at 16 hours of accelerated aging deployed at 3.5 mm.
Stents Deployed to 3.5 mm

| Stent # | Micro | <25% | <50% | >50% |
|---|---|---|---|---|
| 4 | | | | |
| A | 1 | | | |
| B | | | | |
| 5 | | | | |
| A | 7 | | | |
| B | 1 | | | |

TABLE 5B

Number of cracks observed for stents deployed at 4.0 mm for 100:1 stent samples at 16 hours of accelerated aging.
Stents Deployed to 4.0 mm

| Stent # | Micro | <25% | <50% | >50% |
|---|---|---|---|---|
| 1 | | | | |
| A | 6 | 1 | | |
| B | 3 | 1 | | |
| 2 | | | | |
| A | | | | |
| B | 1 | | | |
| 3 | | | | |
| A | 5 | | | 1 |
| B | 1 | | | |

TABLE 5B-continued

Number of cracks observed for stents deployed at 4.0 mm for 100:1 stent samples at 16 hours of accelerated aging.
Stents Deployed to 4.0 mm

| Stent # | Micro | <25% | <50% | >50% |
|---|---|---|---|---|
| 4 | | | | |
| A | 1 | | 1 | |
| B | 2 | | | 1 |
| 5 | | | | |
| A | 4 | 2 | | |
| B | | | 1 | |

EXAMPLE 10

A stent was fabricated from a polymer/bioceramic composite. The matrix was a PLGA copolymer. Calcium sulfate nanoparticles were mixed with the copolymer matrix. The copolymer was 50 wt % L-lactide and 50 wt % glycolide. The ratio of copolymer to particles was 100:3 by weight. The composite was fabricated according to methods described herein. A tube was fabricated from the composite and the tube was radially expanded. The expanded tube was laser cut to form a stent. The expected degradation time for the composite stent is about 3-5 months.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a stent comprising:
    forming a suspension solution including a fluid, a polymer and bioceramic particles, wherein the polymer is dissolved in the fluid, and wherein the bioceramic particles are dispersed in the solution;
    evaporating at least some of the fluid to precipitate at least some of the polymer from the suspension solution, wherein at least some of the bioceramic particles are precipitated with the precipitated polymer to form a composite mixture, the composite mixture comprising the precipitated bioceramic particles dispersed within the precipitated polymer; and
    fabricating a stent from the composite mixture after removing from the suspension solution, wherein fabricating the stent comprises extruding the composite mixture above the melting point (Tm) of the polymer to form a polymer tube, wherein the extruded composite mixture is conveyed through a die and into a water bath at a temperature below 25 deg C., and wherein the stent is fabricated from the tube.

2. The method according to claim 1, further comprising decreasing the pressure above the suspension solution below a vapor pressure of the fluid to facilitate the evaporation.

3. The method according to claim 1, further comprising heating the suspension solution to facilitate the evaporation.

4. The method according to claim 1, wherein the suspension solution comprises a surfactant.

5. The method according to claim 1, wherein the polymer is biodegradable.

6. The method according to claim 1, wherein the bioceramic particles are nanoparticles.

7. The method according to claim 1, wherein all or substantially all of the bioceramic particles are removed from the suspension solution.

8. The method according to claim 1, wherein a ratio of the weight percent of the bioceramic particles to the polymer in the suspension solution is at least 1:200.

9. The method according to claim 1, further comprising treating the bioceramic particles with an adhesion promoter prior to or after forming the suspension solution.

10. The method according to claim 1, wherein the bioceramic particles comprise hydroxyapatite or calcium sulfate.

* * * * *